United States Patent
Lawman et al.

(10) Patent No.: US 10,751,400 B2
(45) Date of Patent: Aug. 25, 2020

(54) DNA VECTOR AND TRANSFORMED TUMOR CELL VACCINES

(71) Applicant: MORPHOGENESIS, INC., Tampa, FL (US)

(72) Inventors: Michael J. P. Lawman, Temple Terrace, FL (US); Patricia D. Lawman, Temple Terrace, FL (US); Vijay Ramiya, Tampa, FL (US); Meghan Gentilini, St. Petersburg, FL (US)

(73) Assignee: MORPHOGENESIS, INC., Tampa, FL (US)

( * ) Notice: Subject to any disclaimer, the term of this patent is extended or adjusted under 35 U.S.C. 154(b) by 0 days.

(21) Appl. No.: 16/551,138

(22) Filed: Aug. 26, 2019

(65) Prior Publication Data

US 2020/0000901 A1    Jan. 2, 2020

Related U.S. Application Data

(60) Division of application No. 15/837,965, filed on Dec. 11, 2017, now Pat. No. 10,391,158, which is a continuation-in-part of application No. 15/418,798, filed on Jan. 30, 2017, now Pat. No. 9,839,680, which is a division of application No. 15/110,248, filed as application No. PCT/US2015/018688 on Mar. 4, 2015, now Pat. No. 9,555,088.

(60) Provisional application No. 61/948,980, filed on Mar. 6, 2014.

(51) Int. Cl.
| | | |
|---|---|---|
| *A61K 39/09* | (2006.01) | |
| *A61K 45/06* | (2006.01) | |
| *A61K 39/00* | (2006.01) | |

(52) U.S. Cl.
CPC ........ *A61K 39/0011* (2013.01); *A61K 39/092* (2013.01); *A61K 45/06* (2013.01); *A61K 2039/5152* (2013.01); *A61K 2039/5156* (2013.01); *A61K 2039/53* (2013.01); *A61K 2039/54* (2013.01); *A61K 2039/552* (2013.01); *A61K 2039/55527* (2013.01); *A61K 2039/55533* (2013.01); *A61K 2039/55538* (2013.01); *A61K 2039/585* (2013.01)

(58) Field of Classification Search
CPC .... A61K 2039/5152; A61K 2039/5156; A61K 2039/53; A61K 2039/54; A61K 2039/55527; A61K 2039/55533; A61K 2039/55538; A61K 2039/585; A61K 39/0011; A61K 39/092; A61K 45/06
See application file for complete search history.

(56) References Cited

U.S. PATENT DOCUMENTS

| | | |
|---|---|---|
| 6,737,521 B1 | 5/2004 | Fischetti et al. |
| 7,094,603 B2 | 8/2006 | Lawman et al. |
| 7,348,015 B2 | 3/2008 | Lawman et al. |
| 7,795,020 B2 | 9/2010 | Lawman et al. |
| 2005/0106130 A1 | 5/2005 | Lawman et al. |
| 2008/0166379 A1 | 7/2008 | Lawman et al. |

FOREIGN PATENT DOCUMENTS

WO    WO 99/36433    7/1999

OTHER PUBLICATIONS

Fischetti, V. A. "M Protein and Other Surface Proteins on Streptococci" *Streptococcus pyogenes: Basic Biology to Clinical Manifestations* [Internet], Feb. 10, 2016, pp. 1-27.
Marr, R. A. et al. "Tumour immunotherapy using an adenoviral vector expressing a membrane-bound mutant of murine TNFα" *Gene Therapy*, 1997, pp. 1181-1188, vol. 4.
Qudrat, A. et al. "Modular assembly of synthetic proteins that span the plasma membrane in mammalian cells" *BMC Biotechnology*, 2016, pp. 1-8, vol. 16, No. 88.
Schulz, G. E. "The structure of bacterial outer membrane proteins" *Biochimica et Biophysica Acta*, 2002, pp. 308-317, vol. 1565.
Yei, S. et al. "Novel membrane-bound GM-CSF vaccines for the treatment of cancer: generation and evaluation of mbGM-CSF mouse B16F10 melanoma cell vaccine" *Gene Therapy*, 2002, pp. 1302-1311, vol. 9.
Hofmann, K. et al. "A Database of Membrane Spanning Protein Segments" *Biol. Chem.*, 1993, p. 1.
Hartas, J. et al. "*Streptococcus pyogenes* strains containing emm12 and emm55 possess a novel gene coding for distantly related SIC protein" *Microbial Pathogenesis*, 1999, pp. 25-33, vol. 26.
Pack, T. D. et al. "Identification of an amino acid signature sequence predictive of protein G-inhibitable IgG$_3$-binding activity in group-A streptococcal IgG-binding proteins" *Gene*, 1996, pp. 65-70, vol. 171.

*Primary Examiner* — Padmavathi Baskar
(74) *Attorney, Agent, or Firm* — Saliwanchik, Lloyd & Eisenschenk

(57) ABSTRACT

Customized whole cell cancer vaccines can be produced from autologous (ex vivo or in situ) or allogeneic human or veterinary patient cell lines. Cells are transformed with *S. pyogenes* DNA that expresses an Emm protein on the cell surface and cytosol. Treatment of cancer patients with an Emm vector vaccine induces an immunologic response to the cancer by enhancing immunogenicity of a tumor. Emm vaccines can be used in patients where the cancer is not identified due to lower tumor burden or used to treat a specific cancer and subsequently treat for a second type that may have arisen through metastasis.

7 Claims, 17 Drawing Sheets
Specification includes a Sequence Listing.

Post treatment 1- after 4 injections
Post treatment 2- after 8 injections

```
Query    1    ATGGCTAAAAATACCACGAATAGACACTATTCGCTTAGAAAATTAAAAACAGGAACGGCT
              ||||||||||||||||||||||||||| ||||||||||||||||||||||||||||||||
Sbjct    1    ATGGCTAAAAATACCACGAATAGACACGATTCGCTTAGAAAATTAAAAACAGGAACGGCT Query    61   TCAGTAGCAGTAGCTTTGACTGTTTTAGGGACAGGACTGGTAGCAGGGCAGACAGTAAAA
              ||||||||||||||||||||||||||||||||||||||||||||||||||||||||||||
Sbjct    61   TCAGTAGCAGTAGCTTTGACTGTTTTAGGGACAGGACTGGTAGCAGGGCAGACAGTAAAA Query    121  GCAAGCCAAACAGAACCATCTCAGACCAATAACAGATTATATCAAGAAAGACAACGTTTA
              |||| |||||||||||||||||||||||||||||||||||||||||||||||||||||||
Sbjct    121  GCAAACCAAACAGAACCATCTCAGACCAATAACAGATTATATCAAGAAAGACAACGTTTA Query    181  CAGGATTTAAAAAGTAAGTTTCAAGACCTGAAAAATCGTTCAGAGGGATACATTCAGCAA
              |||||||||||||||||| |||||||||||||||||||||||||||||||||||||||||
Sbjct    181  CAGGATTTAAAAAGTAAGGTTCAAGACCTGAAAAATCGTTCAGAGGGATACATTCAGCAA Query    241  TACTACGACGAAGAAAAGAACAGTGGAAGTAACTCTAACTGGTACGCAACCTACTTAAAA
              ||||||||||||||||||||||||||||||||||||||||||||||||||||||||||||
Sbjct    241  TACTACGACGAAGAAAAGAACAGTGGAAGTAACTCTAACTGGTACGCAACCTACTTAAAA Query    301  GAATTAAATGACGAATTTGAACAAGCTTATAATGAACTTAGTGGTGATGGTGTaaaaaaa
              ||||||||||||||||||||||||||||||||||||||||||||||||||||||||||||
Sbjct    301  GAATTAAATGACGAATTTGAACAAGCTTATAATGAACTTAGTGGTGATGGTGTAAAAAAA Query    361  TTAGCTGCAAGTTTGATGGAAGAAAGAGTCGCTTTAAGAGACGAAATCGATCagattaag
              ||||||||||||||||||||||||||||||||||||||||||||||||||||||||||||
Sbjct    361  TTAGCTGCAAGTTTGATGGAAGAAAGAGTCGCTTTAAGAGACGAAATCGATCAGATTAAG Query    421  aaaatatcagaagaattaaaaaataagctgagagcaagaagaagaattaaaaaataaa
              ||||||||||||||||||||||||||||||||||||| ||||||||||||||||||||||
Sbjct    421  AAAATATCAGAAGAATTAAAAAATAAGCTGAGAGCAACAGAAGAAGAATTAAAAAATAAA Query    481  aaagaGGAACGTGAGCTTGAGCATGCTGCCTATGCAGCAGATGCAAAGAAACATGAAGAA
              |||||||||||| ||||||||||||||||||||||||| |||||||||||||||||||||
Sbjct    481  AAAGAGGAACGCGAGCTTGAGCATGCTGCCTATGCAGTAGATGCAAAGAAACATGAAGAA Query    541  TATGTCAAATCCATGTCTCTCGTACTAATGGATAAAGAAGAGAGCG-TCATAACTAGA
              ||||||||||||||||||||||| ||||||||||||||||  ||||| |||| ||||||
Sbjct    541  TATGTCAAATCCATGTCTCTCGCTCTAATGGATAAAGAAG-GAGCGCTCATCTACTAGA Query    600  GCAATCATTAGACACGGCTAAAGCTGAGCTTGTTAAAAAGAGCAAGAGTTACAGTTAGT
              ||||||||||||||||||||||||||||||||||||||||||||||||||||||||||||
Sbjct    600  GCAATCATTAGACACGGCTAAAGCTGAGCTTGTTAAAAAGAGCAAGAGTTACAGTTAGT Query    660  CAAAGGCAATCTAGATCaaaaagaaaaagaactagaaaatgaagagctagcgaaagaaag
              ||||||||||||||||||||||||||||||||||||||||||||||||||||||||||||
Sbjct    660  CAAAGGCAATCTAGATCAAAAAGAAAAAGAACTAGAAAATGAAGAGCTAGCGAAAGAAAG Query    720  TGCTATTAGTGATTTGACTGAGCAGATTACTGCTAAGAAGGCTGAAGTAGAAAAATTAAC
              ||||||||||||||||||||||||||||||||||||||||||||||||||||||||||||
Sbjct    720  TGCTATTAGTGATTTGACTGAGCAGATTACTGCTAAGAAGGCTGAAGTAGAAAAATTAAC Query    780  TCAAGATTTAGCTGCTAAGTCTGCTGAAATTCAGGAAAAGAAGCTGAAAAAGATCGCCA
              ||||||||||||||||||||||||||||||||||||||||||||||||||||||||||||
Sbjct    780  TCAAGATTTAGCTGCTAAGTCTGCTGAAATTCAGGAAAAGAAGCTGAAAAAGATCGCCA
```

FIG. 13

```
Query  840   ACAGCATATGTACGAAGCGTTTATGAGCCAGTACAAAGAAAAGTTGAGAAACAAGAGCA
             |||||||||||||||||||||||||||||||||||||||||||||||||||||||||||
Sbjct  840   ACAGCATATGTACGAAGCGTTTATGAGCCAGTACAAAGAAAAGTTGAGAAACAAGAGCA Query  900   AGAGCTTGCTAAGCTAAAACAACTTGAAACCATCAACAACAATCTATTAGGTAATGCTAA
             ||||||||||||||||||||||||||||||||||||||||||||||||||||||||||||
Sbjct  900   AGAGCTTGCTAAGCTAAAACAACTTGAAACCATCAACAACAATCTATTAGGTAATGCTAA Query  960   GGATATGATAGCTAAGTTGTCTGCTGAAAATGAACAATTAGCAAGCGACAAAGCAAAACT
             ||||||||||||||||||||||||||||||||||||||||||||||||||||||||||||
Sbjct  960   GGATATGATAGCTAAGTTGTCTGCTGAAAATGAACAATTAGCAAGCGACAAAGCAAAACT Query  1020  TGAAGAACAAAACAAGATTTCAGAAGCGAGCCGTAAAGGTCTTCGTCGTGACTTGGACGC
             ||||||||||||||||||||||||||||||||||||||||||||||||||||||||||||
Sbjct  1020  TGAAGAACAAAACAAGATTTCAGAAGCGAGCCGTAAAGGTCTTCGTCGTGACTTGGACGC Query  1080  ATCACGTGAAGCTAAGAAACAAGTTGAAAAGATTTAGCAAACTTGACTGCTGAACTTGA
             |||||||||||||||||||||||||||||||||||||||||||||||||||||||||||
Sbjct  1080  ATCACGTGAAGCTAAGAAACAAGTTGAAAAGATTTAGCAAACTTGACTGCTGAACTTGA Query  1140  TAAGGTTAAAGAAGATAAACAAATTTCAGACGCAAGCCGTAAAGGTCTTCGTCGTGACTT
             ||||||||||||||||||||||||||||||||||||||||||||||||||||||||||||
Sbjct  1140  TAAGGTTAAAGAAGATAAACAAATTTCAGACGCAAGCCGTAAAGGTCTTCGTCGTGACTT Query  1200  GGACGCATCACGTGAAGCTAAGAAACAAGTTGAAAAGCTTTAGAAGAAGCAAACAGCAA
             |||||||||||||||||||||||||||||||||||||||||||||||||||||||||||
Sbjct  1200  GGACGCATCACGTGAAGCTAAGAAACAAGTTGAAAAGCTTTAGAAGAAGCAAACAGCAA Query  1260  ATTAGCGGCTCTTgaaaacttaacaaagagcttgaagaagcaagaattaacagaaaa
             ||||||||||||||||||||||||||||||||||||||||||||||||||||||||||
Sbjct  1260  ATTAGCGGCTCTTGAAAACTTAACAAAGAGCTTGAAGAAGCAAGAATTAACAGAAAA Query  1320  agaaaaagCTGAGCTACAAGCGAAACTTGAAGCAGAAGCAAAGCACTCAAAGAACAATT
             ||||||||||||||||||||||||||||||||||||||||||| |||||||||| ||||
Sbjct  1320  AGAAAAAGCTGAGCTACAAGCGAAACTTGAAGCAGAAGCAAAAACACTCAAAGAAAATT Query  1380  AGCGAAACAAGCTGAAGAACTTGCAAAACTAAGAGCTGGAAAAGCATCAGACTCACAAAC
             ||||||||||||||||||||||||||||||||||||||||||||||||||||||||||||
Sbjct  1380  AGCGAAACAAGCTGAAGAACTTGCAAAACTAAGAGCTGGAAAAGCATCAGACTCACAAAC Query  1440  CCCTGATGCAAAACCAGGAAACAAAGTGTTCCAGGTACAGGTCAAGCACCACAAGCAGG
             |||||||||||||||||||||||||||| ||||||||| |||||||||||||||||||
Sbjct  1440  CCCTGATGCAAAACCAGGAAACAAAGCTGTTCCAGGTAAAGGTCAAGCACCACAAGCAGG Query  1500  CACAAAACCTAACCAAAACAAAGCACCAATGAAGGAAACTAAGAGACAGTTACCATCAAC
             ||||||||||||||||||||||||||||||||||||||||||||||||||||||||||||
Sbjct  1500  TACAAAACCTAACCAAAACAAAGCACCAATGAAGGAAACTAAGAGACAGTTACCATCAAC Query  1560  AGGTGAAGCAGCTAATCCATTCTTTACAGCGGCAGCCCTTACTGTTATGGCAACAGCTGG
             ||||||| |||||| ||||||| |||||||||||||||||||||||||||||||||||
Sbjct  1560  AGGTGAAACAGCTAACCCATTCTTCACAGCGGCAGCCCTTACTGTTATGGCAACAGCTGG Query  1620  AGTAGCAGCAGTTGTAAACGCAAAGAAGAAAACGAA    1656
             |||     ||||||||| ||||||||||||||||| ||
Sbjct  1620  AGT----AGCAGTTGTCAAACGCAAAGAAGAAAACTAA   1653
                                                   Stop codon
```

FIG. 13 (continued)

```
                    Signal peptide                              mouse epitope
UserSeq1,   1  MAKNTTNRHYSLRKLKTGIASVAVALTVLGTGLVAGQTVKASQTEPSQTNNRLYQERQRL
UserSeq2,   1  MAKNTTNRHISLRKLKTGIASVAVALTVLGTGLVAGQTVKANQTEPSQTNNRLYQERQRL
               ********* **************************** *********************

UserSeq1,  61  QDLKSKFQDLKNRSEGYIQQYYDEEKNSGSNSNWYATYLKELNDEFEQAYNELSGDGVKK
UserSeq2,  61  QDLKSKVQDLKNRSEGYIQQYYDEEKNSGSNSNWYATYLKELNDEFEQAYNELSGDGVKK
               ****** *****************************************************

UserSeq1, 121  LAASLMEERVALRDEIDQIKKISEELKNKLRAKEEELKNKKEERELEHAAYAADAKKHEE
UserSeq2, 121  LAASLMEERVALRDEIDQIKKISEELKNKLRATEEELKNKKEERELEHAAYAVDAKKHEE
               ******************************** ******************* ******

UserSeq1, 181  YVKSMSLYIMDKEEFRHKLEQSLDTAKAELVKKEQELQLVKGNLDQKEKELENEELAKES
UserSeq2, 181  YVKSMSLALMDKEESAHLLEQSLDTAKAELVKKEQELQLVKGNLDQKEKELENEELAKES
               ******* ****** *  ******************************************
                                        Potential human epitope
UserSeq1, 241  AISDLTEQITAKKAEVEKLTQDLAAKSAEIQEKEAEKDRQQHMYEAFMSQYKEKVEKQEQ
UserSeq2, 241  AISDLTEQITAKKAEVEKLTQDLAAKSAEIQEKEAEKDRQQHMYEAFMSQYKEKVEKQEQ
               ************************************************************

UserSeq1, 301  ELAKLKQLETINNNLLGNAKDMIAKLSAENEQLASDKAKLEEQNKISEASRKGLRRDLDA
UserSeq2, 301  ELAKLKQLETINNNLLGNAKDMIAKLSAENEQLASDKAKLEEQNKISEASRKGLRRDLDA
               ************************************************************

UserSeq1, 361  SREAKKQVEKDLANLTAELDKVKEDKQISDASRKGLRRDLDASREAKKQVEKALEEANSK
UserSeq2, 361  SREAKKQVEKDLANLTAELDKVKEDKQISDASRKGLRRDLDASREAKKQVEKALEEANSK
               ************************************************************

UserSeq1, 421  LAALEKLNKELEESKKLTEKEKAELQAKLEAEAKALKEQLAKQAEELAKLRAGKASDSQT
UserSeq2, 421  LAALEKLNKELEESKKLTEKEKAELQAKLEAEAKILKEKLAKQAEELAKLRAGKASDSQT
               ********************************** *** *********************
                                                        Gm+ve anchor
UserSeq1, 481  PDAKPGNKVVPGTGQAPQAGTKPNQNKAPMTKETKRQLPSTGEAANPFFTAAALTVMATA
UserSeq2, 481  PDAKPGNKAVPGKGQAPQAGTKPNQNKAPM KETKRQLPSTGETANPFFTAAALTVMATA
               ******** *** ***************** *********** ****************

UserSeq1, 541  GVAAVVKRKEENEAEPCRYPSHWRPRL
UserSeq2, 540  GVAJVVRKEEN---------------
               *** ******* absence of stop codon result in continued translation of
additional amino acids of the plasmid frame work till reaches a stop codon TAG.
```

FIG. 14

```
                          SEQUENCE LISTING

<160> NUMBER OF SEQ ID NOS: 9

<210> SEQ ID NO 1
<211> LENGTH: 1656
<212> TYPE: DNA
<213> ORGANISM: Streptococcus pyogenes

<400> SEQUENCE: 1
atggctaaaa ataccacgaa tagacactat tcgcttagaa aattaaaaac aggaacggct      60
tcagtagcag tagctttgac tgttttaggg acaggactgg tagcagggca gacagtaaaa     120
gcaagccaaa cagaaccatc tcagaccaat aacagattat atcaagaaag acaacgttta     180
caggatttaa aaagtaagtt tcaagacctg aaaaatcgtt cagagggata cattcagcaa     240
tactacgacg aagaaaagaa cagtggaagt aactctaact ggtacgcaac ctacttaaaa     300
gaattaaatg acgaatttga acaagcttat aatgaactta gtggtgatgg tgtaaaaaaa     360
ttagctgcaa gtttgatgga agaaagagtc gctttaagag acgaaatcga tcagattaag     420
aaaatatcag aagaattaaa aaataagctg agagcaaaag aagaagaatt aaaaaataaa     480
aaagaggaac gtgagcttga gcatgctgcc tatgcagcag atgcaaagaa acatgaagaa     540
tatgtcaaat ccatgtctct cgtactaatg gataaagaag aggagcgtca taaactagag     600
caatcattag acacggctaa agctgagctt gttaaaaaag agcaagagtt acagttagtc     660
aaaggcaatc tagatcaaaa agaaaaagaa ctagaaaatg aagagctagc gaaagaaagt     720
gctattagtg atttgactga gcagattact gctaagaagg ctgaagtaga aaaattaact     780
caagatttag ctgctaagtc tgctgaaatt caggaaaaag aagctgaaaa agatcgccaa     840
cagcatatgt acgaagcgtt tatgagccag tacaaagaaa aagttgagaa acaagagcaa     900
gagcttgcta agctaaaaca acttgaaacc atcaacaaca atctattagg taatgctaag     960
gatatgatag ctaagttgtc tgctgaaaat gaacaattag caagcgacaa agcaaaactt    1020
gaagaacaaa acaagatttc agaagcgagc cgtaaaggtc ttcgtcgtga cttggacgca    1080
tcacgtgaag ctaagaaaca agttgaaaaa gatttagcaa acttgactgc tgaacttgat    1140
aaggttaaag aagataaaca aatttcagac gcaagccgta aaggtcttcg tcgtgacttg    1200
gacgcatcac gtgaagctaa gaaacaagtt gaaaaagctt tagaagaagc aaacagcaaa    1260
ttagcggctc ttgaaaaact taacaaagag cttgaagaaa gcaagaaatt aacagaaaaa    1320
gaaaaagctg agctacaagc gaaacttgaa gcagaagcaa aagcactcaa agaacaatta    1380
```

```
gcgaaacaag ctgaagaact tgcaaaacta agagctggaa aagcatcaga ctcacaaacc   1440
cctgatgcaa aaccaggaaa caaagttgtt ccaggtacag gtcaagcacc acaagcaggc   1500
acaaaaccta accaaaacaa agcaccaatg aaggaaacta agagacagtt accatcaaca   1560
ggtgaagcag ctaatccatt ctttacagcg gcagccctta ctgttatggc aacagctgga   1620
gtagcagcag ttgtaaaacg caaagaagaa acgaa                             1656
```

<210> SEQ ID NO 2
<211> LENGTH: 567
<212> TYPE: PRT
<213> ORGANISM: Streptococcus pyogenes

<400> SEQUENCE: 2

```
Met Ala Lys Asn Thr Thr Asn Arg His Tyr Ser Leu Arg Lys Leu Lys
1               5                   10                  15

Thr Gly Thr Ala Ser Val Ala Val Ala Leu Thr Val Leu Gly Thr Gly
            20                  25                  30

Leu Val Ala Gly Gln Thr Val Lys Ala Ser Gln Thr Glu Pro Ser Gln
        35                  40                  45

Thr Asn Asn Arg Leu Tyr Gln Glu Arg Gln Leu Gln Asp Leu Lys
    50                  55                  60

Ser Lys Phe Gln Asp Leu Lys Asn Arg Ser Glu Gly Tyr Ile Gln Gln
65                  70                  75                  80

Tyr Tyr Asp Glu Glu Lys Asn Ser Gly Ser Asn Ser Asn Trp Tyr Ala
                85                  90                  95

Thr Tyr Leu Lys Glu Leu Asn Asp Glu Phe Gln Ala Tyr Asn Glu
            100                 105                 110

Leu Ser Gly Asp Gly Val Lys Lys Leu Ala Ala Ser Leu Met Glu Glu
        115                 120                 125

Arg Val Ala Leu Arg Asp Glu Ile Asp Gln Ile Lys Lys Ile Ser Glu
130                 135                 140

Glu Leu Lys Asn Lys Leu Arg Ala Lys Glu Glu Leu Lys Asn Lys
145                 150                 155                 160

Lys Glu Glu Arg Glu Leu Glu His Ala Ala Tyr Ala Ala Asp Ala Lys
                165                 170                 175

Lys His Glu Glu Tyr Val Lys Ser Met Ser Leu Val Leu Met Asp Lys
            180                 185                 190

Glu Glu Glu Arg His Lys Leu Glu Gln Ser Leu Asp Thr Ala Lys Ala
        195                 200                 205

Glu Leu Val Lys Lys Glu Gln Glu Leu Gln Leu Val Lys Gly Asn Leu
    210                 215                 220

Asp Gln Lys Glu Lys Glu Leu Glu Asn Glu Glu Leu Ala Lys Glu Ser
225                 230                 235                 240

Ala Ile Ser Asp Leu Thr Glu Gln Ile Thr Ala Lys Lys Ala Glu Val
                245                 250                 255

Glu Lys Leu Thr Gln Asp Leu Ala Ala Lys Ser Ala Glu Ile Gln Glu
            260                 265                 270

Lys Glu Ala Glu Lys Asp Arg Gln Gln His Met Tyr Glu Ala Phe Met
        275                 280                 285

Ser Gln Tyr Lys Glu Lys Val Glu Lys Glu Gln Glu Leu Ala Lys
    290                 295                 300

Leu Lys Gln Leu Glu Thr Ile Asn Asn Asn Leu Leu Gly Asn Ala Lys
305                 310                 315                 320
```

Asp Met Ile Ala Lys Leu Ser Ala Glu Asn Glu Gln Leu Ala Ser Asp
            325                 330                 335

Lys Ala Lys Leu Glu Glu Gln Asn Lys Ile Ser Glu Ala Ser Arg Lys
        340                 345                 350

Gly Leu Arg Arg Asp Leu Asp Ala Ser Arg Glu Ala Lys Lys Gln Val
    355                 360                 365

Glu Lys Asp Leu Ala Asn Leu Thr Ala Glu Leu Asp Lys Val Lys Glu
370                 375                 380

Asp Lys Gln Ile Ser Asp Ala Ser Arg Lys Gly Leu Arg Arg Asp Leu
385                 390                 395                 400

Asp Ala Ser Arg Glu Ala Lys Lys Gln Val Glu Lys Ala Leu Glu Glu
                405                 410                 415

Ala Asn Ser Lys Leu Ala Ala Leu Glu Lys Leu Asn Lys Glu Leu Glu
            420                 425                 430

Glu Ser Lys Lys Leu Thr Glu Lys Glu Lys Ala Glu Leu Gln Ala Lys
        435                 440                 445

Leu Glu Ala Glu Ala Lys Ala Leu Lys Glu Gln Leu Ala Lys Gln Ala
    450                 455                 460

Glu Glu Leu Ala Lys Leu Arg Ala Gly Lys Ala Ser Asp Ser Gln Thr
465                 470                 475                 480

Pro Asp Ala Lys Pro Gly Asn Lys Val Val Pro Gly Thr Gly Gln Ala
                485                 490                 495

Pro Gln Ala Gly Thr Lys Pro Asn Gln Asn Lys Ala Pro Met Thr Lys
            500                 505                 510

Glu Thr Lys Arg Gln Leu Pro Ser Thr Gly Glu Ala Ala Asn Pro Phe
        515                 520                 525

Phe Thr Ala Ala Ala Leu Thr Val Met Ala Thr Ala Gly Val Ala Ala
    530                 535                 540

Val Val Lys Arg Lys Glu Glu Asn Glu Ala Glu Phe Cys Arg Tyr Pro
545                 550                 555                 560

Ser His Trp Arg Pro Arg Leu
                565

<210> SEQ ID NO 3
<211> LENGTH: 1653
<212> TYPE: DNA
<213> ORGANISM: Streptococcus pyogenes

<400> SEQUENCE: 3

```
atggctaaaa ataccacgaa tagacacgat tcgcttagaa aattaaaaac aggaacggct      60
tcagtagcag tagctttgac tgttttaggg acaggactgg tagcagggca gacagtaaaa     120
gcaaaccaaa cagaaccatc tcagaccaat aacagattat atcaagaaag acaacgttta     180
caggatttaa aaagtaaggt tcaagacctg aaaaatcgtt cagagggata cattcagcaa     240
tactacgacg aagaaaagaa cagtggaagt aactctaact ggtacgcaac ctacttaaaa     300
gaattaaatg cgaatttgaa caagcttat aatgaactta gtggtgatgg tgtaaaaaaa     360
ttagctgcaa gtttgatgga agaaagagtc gctttaagag acgaaatcga tcagattaag     420
aaaatatcag aagaattaaa aataagctg agagcaacag aagaagaatt aaaaaataaa     480
aaagaggaac gcgagcttga gcatgctgcc tatgcagtag atgcaaagaa acatgaagaa     540
tatgtcaaat ccatgtctct cgctctaatg gataaagaag agagcgctca tctactagag     600
caatcattag acacggctaa agctgagctt gttaaaaaag agcaagagtt acagttagtc     660
aaaggcaatc tagatcaaaa agaaaaagaa ctagaaaatg aagagctagc gaaagaaagt     720
```

```
gctattagtg atttgactga gcagattact gctaagaagg ctgaagtaga aaaattaact      780
caagatttag ctgctaagtc tgctgaaatt caggaaaaag aagctgaaaa agatcgccaa      840
cagcatatgt acgaagcgtt tatgagccag tacaaagaaa agttgagaaa caagagcaa       900 gagcttgcta agctaaaaca acttgaaacc atcaacaaca atctattagg taatgctaag      960
gatatgatag ctaagttgtc tgctgaaaat gaacaattag caagcgacaa agcaaaactt     1020
gaagaacaaa acaagatttc agaagcgagc cgtaaaggtc ttcgtcgtga cttgacgca      1080 tcacgtgaag ctaagaaaca agttgaaaaa gatttagcaa acttgactgc tgaacttgat     1140
aaggttaaag aagataaaca aatttcagac gcaagccgta aaggtcttcg tcgtgacttg     1200
gacgcatcac gtgaagctaa gaaacaagtt gaaaaagctt agaagaagc aaacagcaaa      1260 ttagcggctc ttgaaaaact taacaaagag cttgaagaaa gcaagaaatt aacgaaaaa      1320 gaaaaagctg agctacaagc gaaacttgaa gcagaagcaa aaacactcaa agaaaaatta    1380
gcgaaacaag ctgaagaact tgcaaaacta agagctggaa aagcatcaga ctcacaaacc    1440
cctgatgcaa aaccaggaaa caaagctgtt ccaggtaaag gtcaagcacc acaagcaggt    1500
acaaaaccta ccaaaacaa agcaccaatg aaggaaacta agagacagtt accatcaaca    1560
ggtgaaacag ctaacccatt cttcacagcg gcagcccta ctgttatggc aacagctgga      1620
gtagcagttg tcaaacgcaa agaagaaaac taa                                  1653

<210> SEQ ID NO 4
<211> LENGTH: 550
<212> TYPE: PRT
<213> ORGANISM: Streptococcus pyogenes

<400> SEQUENCE: 4

Met Ala Lys Asn Thr Thr Asn Arg His Asp Ser Leu Arg Lys Leu Lys
1               5                   10                  15

Thr Gly Thr Ala Ser Val Ala Val Ala Leu Thr Val Leu Gly Thr Gly
            20                  25                  30

Leu Val Ala Gly Gln Thr Val Lys Ala Asn Gln Thr Glu Pro Ser Gln
        35                  40                  45

Thr Asn Asn Arg Leu Tyr Gln Glu Arg Gln Arg Leu Gln Asp Leu Lys
    50                  55                  60

Ser Lys Val Gln Asp Leu Lys Asn Arg Ser Glu Gly Tyr Ile Gln Gln
65                  70                  75                  80

Tyr Tyr Asp Glu Glu Lys Asn Ser Gly Ser Asn Ser Asn Trp Tyr Ala
                85                  90                  95

Thr Tyr Leu Lys Glu Leu Asn Asp Glu Phe Glu Gln Ala Tyr Asn Glu
            100                 105                 110

Leu Ser Gly Asp Gly Val Lys Lys Leu Ala Ala Ser Leu Met Glu Glu
        115                 120                 125

Arg Val Ala Leu Arg Asp Glu Ile Asp Gln Ile Lys Lys Ile Ser Glu
    130                 135                 140

Glu Leu Lys Asn Lys Leu Arg Ala Thr Glu Glu Leu Lys Asn Lys
145                 150                 155                 160

Lys Glu Glu Arg Glu Leu Glu His Ala Ala Tyr Ala Val Asp Ala Lys
                165                 170                 175

Lys His Glu Glu Tyr Val Lys Ser Met Ser Leu Ala Leu Met Asp Lys
            180                 185                 190

Glu Glu Ser Ala His Leu Leu Glu Gln Ser Leu Asp Thr Ala Lys Ala
        195                 200                 205
```

Glu Leu Val Lys Lys Glu Gln Glu Leu Gln Leu Val Lys Gly Asn Leu
    210                 215                 220

Asp Gln Lys Glu Lys Glu Leu Glu Asn Glu Glu Leu Ala Lys Glu Ser
225                 230                 235                 240

Ala Ile Ser Asp Leu Thr Glu Gln Ile Thr Ala Lys Lys Ala Glu Val
            245                 250                 255

Glu Lys Leu Thr Gln Asp Leu Ala Ala Lys Ser Ala Glu Ile Gln Glu
        260                 265                 270

Lys Glu Ala Glu Lys Asp Arg Gln Gln His Met Tyr Glu Ala Phe Met
    275                 280                 285

Ser Gln Tyr Lys Glu Lys Val Glu Lys Gln Glu Gln Glu Leu Ala Lys
290                 295                 300

Leu Lys Gln Leu Glu Thr Ile Asn Asn Asn Leu Leu Gly Asn Ala Lys
305                 310                 315                 320

Asp Met Ile Ala Lys Leu Ser Ala Glu Asn Glu Gln Leu Ala Ser Asp
            325                 330                 335

Lys Ala Lys Leu Glu Glu Gln Asn Lys Ile Ser Glu Ala Ser Arg Lys
        340                 345                 350

Gly Leu Arg Arg Asp Leu Asp Ala Ser Arg Glu Ala Lys Lys Gln Val
    355                 360                 365

Glu Lys Asp Leu Ala Asn Leu Thr Ala Glu Leu Asp Lys Val Lys Glu
370                 375                 380

Asp Lys Gln Ile Ser Asp Ala Ser Arg Lys Gly Leu Arg Arg Asp Leu
385                 390                 395                 400

Asp Ala Ser Arg Glu Ala Lys Lys Gln Val Glu Lys Ala Leu Glu Glu
            405                 410                 415

Ala Asn Ser Lys Leu Ala Ala Leu Glu Lys Leu Asn Lys Glu Leu Glu
        420                 425                 430

Glu Ser Lys Lys Leu Thr Glu Lys Glu Lys Ala Glu Leu Gln Ala Lys
    435                 440                 445

Leu Glu Ala Glu Ala Lys Thr Leu Lys Glu Lys Leu Ala Lys Gln Ala
450                 455                 460

Glu Glu Leu Ala Lys Leu Arg Ala Gly Lys Ala Ser Asp Ser Gln Thr
465                 470                 475                 480

Pro Asp Ala Lys Pro Gly Asn Lys Ala Val Pro Gly Lys Gly Gln Ala
            485                 490                 495

Pro Gln Ala Gly Thr Lys Pro Asn Gln Asn Lys Ala Pro Met Lys Glu
        500                 505                 510

Thr Lys Arg Gln Leu Pro Ser Thr Gly Glu Thr Ala Asn Pro Phe Phe
    515                 520                 525

Thr Ala Ala Ala Leu Thr Val Met Ala Thr Ala Gly Val Ala Val Val
530                 535                 540

Lys Arg Lys Glu Glu Asn
545                 550

<210> SEQ ID NO 5
<211> LENGTH: 564
<212> TYPE: PRT
<213> ORGANISM: Streptococcus pyogenes

<400> SEQUENCE: 5

Met Ala Lys Asn Thr Thr Asn Arg His Tyr Ser Leu Arg Lys Leu Lys
1               5                   10                  15

Thr Gly Thr Ala Ser Val Ala Val Ala Leu Thr Val Leu Gly Thr Gly

```
            20                  25                  30
Leu Val Ala Gly Gln Thr Val Lys Ala Ser Gln Thr Glu Pro Ser Gln
            35                  40                  45

Thr Asn Asn Arg Leu Tyr Gln Glu Arg Gln Arg Leu Gln Asp Leu Lys
            50                  55                  60

Ser Lys Phe Gln Asp Leu Lys Asn Arg Ser Glu Gly Tyr Ile Gln Gln
65                  70                  75                  80

Tyr Tyr Asp Glu Lys Asn Ser Gly Ser Asn Ser Asn Trp Tyr Ala
                85                  90                  95

Thr Tyr Leu Lys Glu Leu Asn Asp Glu Phe Glu Gln Ala Tyr Asn Glu
                100                 105                 110

Leu Ser Gly Asp Gly Val Lys Lys Leu Ala Ala Ser Leu Met Glu Glu
            115                 120                 125

Arg Val Ala Leu Arg Asp Glu Ile Asp Gln Ile Lys Lys Ile Ser Glu
            130                 135                 140

Glu Leu Lys Asn Lys Leu Arg Ala Lys Glu Glu Leu Lys Asn Lys
145                 150                 155                 160

Lys Glu Glu Arg Glu Leu Glu His Ala Ala Tyr Ala Ala Asp Ala Lys
                165                 170                 175

Lys His Glu Glu Tyr Val Lys Ser Met Ser Leu Val Leu Met Asp Lys
            180                 185                 190

Glu Glu Glu Arg His Lys Leu Glu Gln Ser Leu Asp Thr Ala Lys Ala
            195                 200                 205

Glu Leu Val Lys Lys Glu Gln Glu Leu Gln Leu Val Lys Gly Asn Leu
            210                 215                 220

Asp Gln Lys Glu Lys Glu Leu Asn Glu Glu Leu Ala Lys Glu Ser Ala
225                 230                 235                 240

Ile Ser Asp Leu Thr Glu Gln Ile Thr Ala Lys Lys Ala Glu Val Glu
                245                 250                 255

Lys Leu Thr Gln Asp Leu Ala Ala Lys Ser Ala Glu Ile Gln Glu Lys
            260                 265                 270

Glu Ala Glu Lys Asp Arg Gln Gln His Met Tyr Glu Ala Phe Met Ser
            275                 280                 285

Gln Tyr Lys Glu Lys Val Glu Lys Gln Glu Gln Glu Leu Ala Lys Leu
            290                 295                 300

Lys Gln Leu Glu Thr Asn Asn Leu Leu Gly Asn Ala Lys Asp Met
305                 310                 315                 320

Ile Ala Lys Leu Ser Ala Glu Asn Glu Gln Leu Ala Ser Asp Lys Ala
                325                 330                 335

Lys Leu Glu Glu Gln Asn Lys Ile Ser Glu Ala Ser Arg Lys Gly Leu
            340                 345                 350

Arg Arg Asp Leu Asp Ala Ser Arg Glu Ala Lys Lys Gln Val Glu Lys
            355                 360                 365

Asp Leu Ala Asn Leu Thr Ala Glu Leu Asp Lys Val Lys Glu Asp Lys
            370                 375                 380

Gln Ile Ser Asp Ala Ser Arg Lys Gly Leu Arg Arg Asp Leu Asp Ala
385                 390                 395                 400

Ser Arg Glu Ala Lys Lys Gln Val Glu Lys Ala Leu Glu Glu Ala Asn
                405                 410                 415

Ser Lys Leu Ala Ala Leu Glu Lys Leu Asn Lys Glu Leu Glu Glu Ser
            420                 425                 430

Lys Lys Leu Thr Glu Lys Glu Lys Ala Glu Leu Gln Ala Lys Leu Glu
            435                 440                 445
```

Ala Glu Ala Lys Ala Leu Lys Glu Gln Leu Ala Lys Gln Ala Glu Glu
            450                 455                 460

Leu Ala Lys Leu Arg Ala Gly Lys Ala Ser Asp Ser Gln Thr Pro Asp
465                 470                 475                 480

Ala Lys Pro Gly Asn Lys Val Val Pro Gly Thr Gly Gln Ala Pro Gln
                485                 490                 495

Ala Gly Thr Lys Pro Asn Gln Asn Lys Ala Pro Met Lys Glu Thr Lys
            500                 505                 510

Arg Gln Leu Pro Ser Thr Gly Glu Ala Ala Asn Pro Phe Phe Thr Ala
            515                 520                 525

Ala Ala Leu Thr Val Met Ala Thr Ala Gly Val Ala Val Val Lys
            530                 535                 540

Arg Lys Glu Glu Asn Glu Ala Glu Phe Cys Arg Tyr Pro Ser His Trp
545                 550                 555                 560

Arg Pro Arg Leu

<210> SEQ ID NO 6
<211> LENGTH: 41
<212> TYPE: PRT
<213> ORGANISM: Streptococcus pyogenes

<400> SEQUENCE: 6

Met Ala Lys Asn Thr Thr Asn Arg His Tyr Ser Leu Arg Lys Leu Lys
1               5                   10                  15

Thr Gly Thr Ala Ser Val Ala Val Ala Leu Thr Val Leu Gly Thr Gly
            20                  25                  30

Leu Val Ala Gly Gln Thr Val Lys Ala
        35                  40

<210> SEQ ID NO 7
<211> LENGTH: 19
<212> TYPE: PRT
<213> ORGANISM: Streptococcus pyogenes

<400> SEQUENCE: 7

Gly Thr Ala Ser Val Ala Val Ala Leu Thr Val Leu Gly Thr Gly Leu
1               5                   10                  15

Val Ala Gly

<210> SEQ ID NO 8
<211> LENGTH: 38
<212> TYPE: PRT
<213> ORGANISM: Streptococcus pyogenes

<400> SEQUENCE: 8

Lys Arg Gln Leu Pro Ser Thr Gly Glu Ala Ala Asn Pro Phe Phe Thr
1               5                   10                  15

Ala Ala Ala Leu Thr Val Met Ala Thr Ala Gly Val Ala Ala Val Val
            20                  25                  30

Lys Arg Lys Glu Glu Asn
        35

<210> SEQ ID NO 9
<211> LENGTH: 18
<212> TYPE: PRT
<213> ORGANISM: Streptococcus pyogenes

<400> SEQUENCE: 9

-continued

```
Phe Phe Thr Ala Ala Ala Leu Thr Val Met Ala Thr Ala Gly Val Ala
1               5                   10                  15

Ala Val
```

DNA VECTOR AND TRANSFORMED TUMOR CELL VACCINES

CROSS-REFERENCE TO RELATED APPLICATIONS

This application is a divisional of U.S. application Ser. No. 15/837,965, filed Dec. 11, 2017, now U.S. Pat. No. 10,391,158, which is a continuation-in-part of U.S. application Ser. No. 15/418,798, filed Jan. 30, 2017, now U.S. Pat. No. 9,839,680, which is a divisional of U.S. application Ser. No. 15/110,248, filed Jul. 7, 2016, now U.S. Pat. No. 9,555,088, which is the U.S. national stage application of International Patent Application No. PCT/US2015/018688, filed Mar. 4, 2015, which claims the benefit of U.S. Provisional Patent Application No. 61/948,980, filed Mar. 6, 2014.

The Sequence Listing for this application is labeled "Seq-List.txt" which was created on Jun. 18, 2019 and is 21 KB. The entire content of the sequence listing is incorporated herein by reference in its entirety.

The field of the invention relates to therapeutic DNA vector vaccines and particularly to cancer cells transformed in vitro or in vivo with the vector. When the vector is administered in vivo into solid cancers, the polypeptide expressed by the vector enhances or augments an immune response to targeted cancers. The DNA vectors function as vaccines when administered directly to solid cancers or after transformation of isolated cancer cells prepared in vitro from a cancer patient are injected into the patient as whole cell vaccines to treat a broad range of cancers, including multiple liquid and solid tumors.

BACKGROUND OF THE INVENTION

Multiple treatment modalities are available for treating cancer. They include surgical resection of the tumor, chemotherapy, radio therapies and combination therapies. While resection can be curative, tumors recur in most cases. Chemotherapies utilize drugs that kill tumor cells by intercalation of DNA, inhibition of replication, or prevention of microtubule assembly. To avoid killing healthy cells, a balance must be achieved by fine tuning the chemotherapy doses and regimens, which should be based on the type of tumor, stage, grade and overall tumor burden. Radiotherapy is essentially geared to kill cancer cells by damaging DNA. Both chemo and radiotherapies result in a number of side effects in patients, including resistance to therapies, and in most cases, tumors recur.

Conventional treatments for solid and circulating and liquid cancers typically include chemotherapy and/or surgery. Recently there has been interest in developing vaccines in an effort to stimulate an immune defense. It is believed that vaccination against tumors may result in protection from tumor recurrence due to immunological memory.

Recently, interest in immunotherapies based on cancer vaccines has prompted attempts to develop such vaccines as an additional treatment option for cancer patients. Several types of cancer vaccines have been considered, including whole cell, defined tumor antigens, peptides and DNA vaccines. Except for whole cell vaccines, all other vaccines require a thorough understanding of the tumor antigen(s) involved. The non-whole cell vaccines, such as peptide or whole protein vaccines or antigen-specific DNA vaccines require a substantial knowledge of the expression of those tumor antigens, and their immunogenicity in cancer patients. Acquiring such data involves substantial investment in defining the tumor antigens. Besides, most of these types of vaccines involve usage of one tumor antigen (e.g., telomerase antigen, prostatic acid phosphatase). The anti-tumor immunity is complex, and multiple antigens and multiple epitopes are likely to be involved for efficacious clinical outcome. In almost all cancers except the ones induced by viruses, the tumor antigens are mostly self-proteins which have been tolerized during the development of the immune system, and hence it is difficult to induce an immune response against them. In the absence of a clear cut understanding of all tumor antigens involved in breaking self-tolerance and in the induction of clinically relevant immunity against cancer tissue, whole cell vaccines become good candidates for presenting a plethora of tumor antigens to the immune system, thereby hedging against tolerogenic epitopes.

Several cancer vaccines have been tested in clinical trials, either alone or in conjunction with various adjuvants. Unfortunately, the clinical efficacy has thus far not been impressive. Nevertheless, with respect to defined vs non-defined (whole cell) vaccines, the whole cell vaccines appear to be superior.

Tumor antigen vaccines generally show poor antigenicity due to immune tolerance. Most require interventional therapies in order to provide an adequate "danger" signal to the immune system in order to activate a robust, clinically meaningful antitumor immunity.

The adaptive immune response to tumors alone is poor, mostly because the target antigens are self-proteins, except in cases of tumor induced by viruses. Since the immune system has evolved to recognize microbial/pathogenic organisms, it is possible that when self-antigens are presented by antigen presenting cells (APCs), there is normally no "danger" signal, and the APCs therefore provide tolerizing signals to avoid autoimmunity. In the presence of microbial antigens, such as Emm protein, which when expressed in tumor cells, processed and presented by the APCs, is perceived by the adaptive immune system as a "danger" signal. Mature APCs present antigens to T cells, which generate activated MEW class I restricted CD8+ and class II restricted CD4+ cells and results in a clinically effective anti-tumor immunity.

Several similar types of cancer vaccines have been tested in pre-clinical and clinical studies, but thus far only one cancer vaccine, Provenge® (Sipuleucel T, Dendreon Corporation), has been approved by the FDA and only for a single indication; i.e., for use in asymptomatic or minimally symptomatic castration resistant prostate cancer patients.

Provenge® is manufactured by "feeding" patient's APCs in vitro with prostatic acid phosphatase fused to GM-CSF (adjuvant) to induce maturation of APCs, which then stimulate the immune system after infusion into the patient. Provenge® is antigen specific and cannot be employed universally against other types of cancers. The survival benefit with Provenge® averages 4.1 months (Kantoff P W et al., N Engl J Med 2010; 363:411-22).

Autologous whole cell vaccines have been reported, including GVAX vaccine for colorectal cancer. Isolated autologous tumor cells were mixed with *Bacillus* Calmette-Guerin (BCG) as the adjuvant and administered to cancer patients. While some limited clinical activity was observed, it did not reach statistical significance. There was no difference in time to relapse or overall survival (OS). The ulceration induced at the vaccine site by BCG was a substantial issue. Additionally, the FDA requirement for a sterility test could not be fulfilled due to the nature of the tissue leading to premature termination of a Phase III trial.

Some success has been reported with an autologous whole cell vaccine against canine lymphoma (U.S. Pat. No. 7,795, 020). Cancer cells from a solid lymphoma tumor were isolated, transformed in vitro with a vector expressing Emm55 protein on the lymphoma cell surface, and administered to the subject from whom the lymphoma cells were isolated.

While whole cell vaccines have been demonstrated to have clinical activity, manufacturing this type of vaccine requires surgical removal of patient's palpable lymph node, ex vivo processing of cells, transformation of cells with Emm protein, irradiation of tumor cells, and the quality control (QC) of the vaccine for individual patients. With solid tumors, it may be difficult to obtain sufficient cells for processing, and processing can require from one to several weeks.

Autologous melanoma and renal cell carcinoma (RCC) in combination with BCG have been tested in patients (Baars A et al., Ann Oncol (2000) 11:965-970; de Gurijil et al., Cancer Immunol Immunother (2008) 57:1569-1577). A slight improvement in 5 year OS of 33% vs 35% for melanoma and 77% vs 68% for RCC over the historic control, respectively, were observed. Unfortunately, due to ulceration at the vaccination site, BCG was disqualified. Additional trials were conducted with a BCG replacement, hypo-methylated bacterial CpG DNA, in an attempt to prove equivalency with BCG in RCC patients. With a 20% clinical response rate, the authors concluded that equivalency was demonstrated with CpG.

Regardless of some positive results, the potential side effects of CpG caused concern. The safety profile of CpG was investigated in rodents, nonhuman primates and humans. Safety issues included the possibility that CpG might increase host susceptibility to autoimmune disease or predispose to toxic shock. The immune stimulation elicited by CpG motifs can reduce the apoptotic death of stimulated lymphocytes, induce polyclonal B-cell activation and increase the production of autoantibodies and proinflammatory cytokines, all of which are known to increase the risk of autoimmune disease, especially in organ-specific autoimmune diseases. The organ-specific autoimmune diseases are typically promoted by the type of Th1 response preferentially elicited by CpG. For example, in an IL-12-dependent model of experimental allergic encephalomyelitis (that mimics multiple sclerosis), animals treated with CpG and then challenged with autoantigen developed autoreactive Th1 effector cells that caused disease, whereas mice injected with autoantigen alone remained disease free.

A more classic vaccination approach was based on stimulation of the immune system by administering an immunogenic foreign protein. In a molecular mimicry model, CpG was co-administered with *Chlamydia*-derived antigen. Unfortunately, this promoted the induction of autoimmune myocarditis (Bachmaier K et al., Science, 1999; 283:1335-1339). CpG also increased the susceptibility of mice to interventions that can induce arthritis. These results indicated that CpG adjuvant promotes the development of deleterious autoimmune reactions under certain circumstances. This concern was heightened when a clinical trial using CpG as an adjuvant for the hepatitis vaccine was halted after one subject developed Wegener's granulomatosis, an autoimmune disease characterized by inflammation of the vasculature. In addition to the risk of autoimmunity, several studies noted an elevation in the frequency and/or severity of local adverse events (injection site reactions such as pain, swelling, induration, pruritus and erythema) and systemic symptoms (including flu-like symptoms) by CpG-adjuvanted vaccines.

Another approach to cancer vaccines has been to mix cell lines of a selected type of cancer derived from different individuals of the same cancer. An allogeneic pancreatic cancer cell line expressing the adjuvant GM-CSF was used in a phase I clinical trial following pancreaticoduodenoectomy. The administered cells proved to be non-toxic but delayed type hypersensitivity (DTH) reaction in the recipients was observed (Jaffe, E M et al., J. Clin. Oncol. 2001, 19, 145-156).

In other studies using allogeneic cells, a prostate cancer trial employed a mixture of 3 different allogeneic prostate cancer cell lines with BCG. Time to progression improved from 28 to 58 weeks. With prostate GVAX allogeneic vaccine (a mixture of LNCaP and PC-3 cell lines expressing GM-CSF), two clinical trials were conducted—VITAL-1 and VITAL-2. In VITAL 1 trial in hormone resistant prostate cancer patients that compared GVAX against docetaxel, no difference between the groups was found. The VITAL 2 trial that compared GVAX+docetaxel against docetaxel had to be terminated due to safety concerns. The adjuvant GM-CSF, an FDA approved drug capable of stimulating white blood cell growth, has been widely used in cancer vaccine trials with varying results.

DNA vaccines have been the subject of a few limited studies. Plasmid DNA vaccines are circular DNA encoding one or more tumor associated antigens (TAAs) and immune-stimulating or co-stimulating molecules, which are administered intramuscularly, intranodally or intratumorally. The local tissue specific cells and the APCs at the injection site then express the antigens to stimulate the immune system. It is believed that the cross-presentation of antigens by the APCs will be the most important factor in the induction of robust anti-tumor response with DNA vaccines. While safety and efficacy of naked plasmid vaccines have been tested in only a small number of clinical settings, at least the intramuscular, intranodal or intratumoral vaccinations have been shown to be safe and capable of eliciting immune responses to some extent in a few patients.

Naked plasmid DNA vaccines used in clinical settings include constructs coding for TAAs. For example, in cohorts of: 1) B-cell lymphoma patients—TAA: idiotypic determinants; 2) melanoma patients TAAs: gp100, MART-1-derived peptides and tyrosinase or tyrosinase-derived peptides; 3) colorectal carcinoma patients—TAA: carcinoembryonic antigen and CEA; 4) HPV-16+ cervical intraepithelial neoplasia (CIN) patients—TAA: HPV-16 E6; and 5) individuals affected by prostate carcinoma—TAA: prostate specific antigen (PSA) have been tested or are being studied. While the results of these trials are mostly not yet available, they are geared towards specific cancers, and cannot be used in multiple tumors because they depend on TAAs.

SUMMARY OF THE INVENTION

Vaccines provide protection by stimulating immunogenic responses in the body typically generated by administering a substance consisting of an immunogenic material associated with the cause of the disease. Cancers differ from externally invasive bacterial, viral and fungal diseases in that they arise in vivo from natural cells. In theory, vaccines consisting of tumor antigens might be useful if such antigens could be identified for all cancer types; however, identification of these antigens is limited.

The natural immunogenicity of a unique M type protein encoded by a *Streptococcus* gene was used to engineer whole tumor cells to act as an immunogenic primer for tumor antigens in vivo. The therapeutic DNA vectors of the present invention contain a *Streptococcus* emm gene. For example, emm gene from *Streptococcus pyogenes* serotype 55 encodes the Emm protein, an M type polypeptide that is highly immunogenic in canines and humans and likely to be in other species. One can construct an expression vector with an emm gene from any one of several *Streptococcus* M-types by operatively linking the appropriate emm gene insert with a promoter in a mammalian expression vector. The use of this type of DNA vector is exemplified with the plasmid vector pAc/emm which can transform mammalian cells to express the immunogenic Emm polypeptide.

Using an emm DNA vector as an example, customized Emm "vaccines" responsive to a specific cancer or to several types of cancers, depending on the source and type of cancer have been formulated as described herein. When the original cancer source is a solid tumor, cells are isolated from the tumor and subjected to enzymatic digestion prior to culturing and transforming the tumor cells. The transformed cells are then administered to the patient from whom the cancer cells were isolated, thereby acting as an autologous vaccine.

Therapeutic treatment of solid tumors is exemplified with the emm DNA family of vaccines described here. The expression of Emm or other M type proteins in tumor cells enhances immunogenicity. Innate and adaptive anti-tumor immunity is activated in vivo when tumor cells transfected with an appropriate emm DNA vector are administered to a mammal having the same tumor type. The result is a clinically meaningful response against tumor cells, including tumor regression or prevention of recurrence.

The Emm proteins, the immunogen described herein, are generally known as M type proteins. The M protein is a fibrillar coiled-coil dimer that extends from the bacterial cell wall, and is considered an archetypal Gram-positive surface protein. The M protein is a key virulence factor and an immunogen and therefore has been a major target for Group A *Streptococcus* (GAS) vaccine development. Many M proteins contain variable A and B repeats while all contain conserved C repeats. It is also likely that the epitopes that reside within variable, hypervariable and conserved regions of M protein have been preserved across multiple M proteins. Therefore, even if all the M proteins do not have the same amino acid sequence, many of them could be used as demonstrated with Emm.

Most of the M protein sequence consists of heptad repeat motifs in which the first and fourth amino acids are typically hydrophobic, and are core stabilizing residues within the coiled coil (McNamara et al., Science, 2008, 319). Heterogeneity in the amino acid sequence of the N terminal part of M protein, resulting in antigenic diversity (>200), forms the basis of GAS Emm-typing. The size of the predicted mature form of M protein was highly variable and the M protein sequence is heterogeneous, ranging from 229 to 509 residues. Importantly, M protein length was highly correlated with Emm pattern. For instance, M proteins of pattern A-C were the longest (average 443 residues), followed by pattern D (average 360 residues), while those of pattern E were the shortest (average 316 residues 320).

An important aspect of the invention is direct vaccination with a therapeutic DNA vector. The emm DNA vector expressing an immunogenic polypeptide is injected into a solid cancer. The DNA vector enters the tumor cells in vivo and expresses a highly immunogenic polypeptide. The polypeptide stimulates an immune response in vivo to that cancer, acting as an internally generated immuno-stimulant. A DNA plasmid vector such as pAc/emm is injected into the solid tumor. The vector transforms the cancer cells in the tumor which then express the encoded Emm polypeptide. The transformed cancer cells thus become in vivo/in situ vaccines against the tumor cells. Use of therapeutic DNA vectors avoids having to isolate, culture and transform tumor cells in vitro because the vectors can be introduced directly into a solid tumor mass.

Autologous vaccines can also be prepared from the described Emm therapeutic vectors. Cancer cells are isolated from a patient, cultured and transformed in vitro with the vector. The autologous transformed cells are administered to the cancer patient, typically by injection. An immune response to the cancer in the patient is generated.

There are several variations of cell-based M-type polypeptide vaccines which can significantly improve an immune response to cancer cells. The vaccines can be utilized to augment or enhance conventional anti-cancer treatments either as a primary or an adjuvant treatment. Given that there are >200 different M type proteins, variants of an Emm or M type vaccines can be produced which will generate an immune response to tumor cells.

Individualized "custom" autologous tumor vaccines can be prepared by isolating and culturing solid, liquid or metastatic tumor cells from one patient. The cells are transfected in vitro with an emm plasmid which expresses Emm protein on the cell surface and in the cytosol. A vaccine composition prepared from the transformed cells is administered to the patient. The immune system responds to the cancer cells as foreign.

More universal versions of Emm and other M-type vaccines can be prepared by transforming cell cultures of cancer cells isolated from different individuals having the same type of cancer. Allogeneic tumor specific cell lines can be transfected in vitro with emm vector to provide a tumor specific vaccine for administration. The cell lines can be derived from many individuals (allogeneic cell lines) to prepare vaccines by mixing 2 or more cell lines of that cancer. The mixed cancer cell lines are transfected in vitro to express Emm or other related M-type polypeptides, formulated into a vaccine and administered to patients. The allogeneic vaccines can be readily prepared for any solid, liquid or metastatic cancers by having cell lines from these cancer tissues, and mixing 2 or more cell lines of a specific cancer for transformation and administration of the vaccines into cancer patients having that specific type of cancer.

For treatment of cancer patients, the emm therapeutic vector can be directly administered into the tumor; alternatively, any stage or grade of cancer can be treated with allogeneic whole cell vaccines, so long as immune system has not been compromised, preferably in conjunction with chemotherapies that are known to induce immunogenic cell death of cancer cells. In patients with lower grade and early stages of cancer, vaccines can be used as mono therapy.

With the direct DNA vaccine, injections can be administered directly into tumor lesions using lipid reagents, needless injectors, multi-needle administration patches, in vivo electroporation, J-tip, into palpable tissue, or visceral tumor lesions with the guidance of computed tomography (CT) or ultrasound. In using the direct administration of the DNA vector, there is no need to harvest tumor cells from the patient. Processing the cells, transformation and irradiation steps are not required so that expense is reduced and efficiency increased compared with the in vitro process of preparing the cancer vaccine ex vivo.

There are several advantages to the use of allogeneic vaccine cells. The use of antigenically/cytogenetically well-defined cell lines provides access to a sustained and virtually limitless source of TAAs. Cell lines can be highly standardized and are suitable for large-scale production of allogeneic vaccines. Single batches of allogeneic vaccines for all vaccines, independent of HLA haplotype, eliminates variability in the quality and composition of the vaccines and facilitates reliable comparative analysis of clinical outcome, and also eliminates the need for continuous production of tailor-made individual vaccines. Overall, batch production of allogeneic vaccines simplifies the logistics, reduces the labor intensity of vaccine production, simplifies quality assurance processes, delivery process, and increases cost-effectiveness.

Vaccines produced from transformed allogeneic cell lines will have broad application both prophylactically and therapeutically. For a universal Emm vaccine, cell lines can be developed from solid tumors, liquid tumors, metastatic or circulating cancer cells and can be derived from many different individuals. A cocktail of the different transformed cancer cell lines can be formulated into a vaccine for that particular cancer indication. Such a heterologous Emm vaccine can be prepared from the same cancers or different types of cancers from several subjects.

The described customized and individualized vaccines provide a tool for personalized medicine because an Emm vaccine can be developed for a specific cancer in a subject. As a tumor evolves into antigenically distinct cell types due to a progressive accumulation of mutations, tumor cells can evade existing antitumor immunity that had been previously induced by initial vaccine treatment. In such situations, additional vaccines targeting those tumor cells can be readily produced.

Checkpoint inhibitors are antibodies or siRNAs that can be developed and used to revert immune exhausted T cells into activated T cells within the tumor bed that would be clinically beneficial. Agonistic antibodies or immuno-stimulants are reagents that can augment anti-tumor immunity. The disclosed Emm cancer vaccines can also be used in conjunction with monoclonal antibodies to checkpoint inhibitory molecules such as CTLA-4, PD-1, PD-L1, PD-L2, LAG3, TIM3, TIGIT, antibodies to costimulatory molecules such as CD40, OX40, antibodies capable of regulating T regs such as anti-GITR and pan anti-BCL-2, or cytokines such as IL-2, TNF-$\alpha$, IFN-$\gamma$, IFN-$\beta$, and TLR agonists.

A unique transmembrane (TM) sequence is located within the anchor region of the Emm55 protein. While this TM sequence is present in many other M proteins, it is not present in other proteins or in other species. This unique TM can anchor the Emm55 protein on mammalian cell surfaces (FIGS. 4 and 5). Therefore, the TM sequence described here can be used for surface expression of proteins in general, and specifically, when high levels of secreted proteins prove toxic or when stable cell surface expression is considered necessary for stimulation/activation of cells. For example, by limiting expression only to the cell surface using TM sequences, membrane bound GM-CSF and TNF-$\alpha$ have demonstrated anti-tumor activity without cytokine mediated toxicities. In general, TM regions are membrane-spanning domains that consist of a continuous stretch of 20-30 nonpolar residues with a predominance of aliphatic side chains at the center and aromatic residues at both ends. The TM forms the basic structure for anchoring cell surface proteins in the cell wall or plasma membrane. TM regions are also responsible for egress from the cytoplasm to the surface. Surface proteins represent more than 50% of all currently available drug targets. About 25-30% of all proteins are located on membranes. In general, TM domains can be classified into ß-sheet barrels or as $\alpha$-helical forms, both in prokaryotes and eukaryotes. In $\alpha$-helices, the main chain amides are all locally complemented so that the surface contacting the nonpolar membrane interior is exclusively formed by the nonpolar side chains, suggesting the usefulness of an $\alpha$-helix as a membrane-crossing element. While the proteins of the cytoplasmic membrane consist mostly of TM $\alpha$-helices, the ß-barrel TM proteins are found in outer membranes of gram-negative bacteria, the cell wall of gram-positive bacteria, and outer membranes of mitochondria and chloroplasts.

Proteins are targeted to the endoplasmic reticulum (ER) membrane through an N-terminal TM region. With the presence of a peptidase cleavage site downstream of the TM, the protein has enhanced exit capabilities from the ER, and with the further addition of a second TM region, the protein can efficiently anchor and accumulate in the plasma membrane. Surface proteins can be grouped as Polytopic, with multiple membrane spanning domains; e.g., G proteins and Bitopic, with a single membrane spanning region; e.g., receptor tyrosine kinases, immunoglobulin superfamily receptors, integrins, plexins, syndecans, neuropilins, and cadherin).

The entire anchor region of Emm55 protein, which includes the TM domain, can be described based on the deduced structure of M6, the M protein from another serotype of Group A Strep, i.e., a Gram positive bacterial cell wall protein similar to Emm55. The N-terminal portion of the protein is exposed outside the wall as coiled coil $\alpha$-helical dimer rods containing sequence repeat blocks. The anchor region which "anchors" the protein to the cell wall contains Pro/Gly followed by a 19 AA hydrophobic region. A highly conserved heptad peptide motif, LPXTG, is located within this region (FIG. 18). The $\alpha$-helical TM domain is located within this anchor region as shown in the Emm55 primary sequence (FIG. 16, SEQ ID NO: 5).

The prokaryotic TM domain of Emm55 is expected to be useful particularly in the design of fusion products. Examples would include the ability to:

Create synthetic fusion product(s) from non-trans-membrane proteins.

Create fusion products from biologically active compounds, proteins, or drugs in order to disrupt functional intracellular or other transmembrane activities.

Create fusion products from biologically active compounds, proteins, or drugs to enhance functional intracellular and extracellular activities.

BRIEF DESCRIPTION OF THE FIGURES

FIG. 13 shows a nucleotide sequence alignment between the subject application (Query, SEQ ID NO: 1) and the emm55 sequence (Sbjct, SEQ ID NO: 3). The differences have been indicated by the boxes. Transversion mutations=7. Transitional mutations=9. Insertional mutations in Query 1=4. Deletional mutations in Query 1=1.

FIG. 14 shows an amino acid sequence alignment between the subject application (UserSeq1, SEQ ID NO: 2) and the original emm55 sequence (UserSeq2, SEQ ID NO: 4). 97.1% identity in 552 residues overlap; Score: 2591.0; Gap frequency: 0.4%.

DETAILED DESCRIPTION OF THE INVENTION

Figure 1:
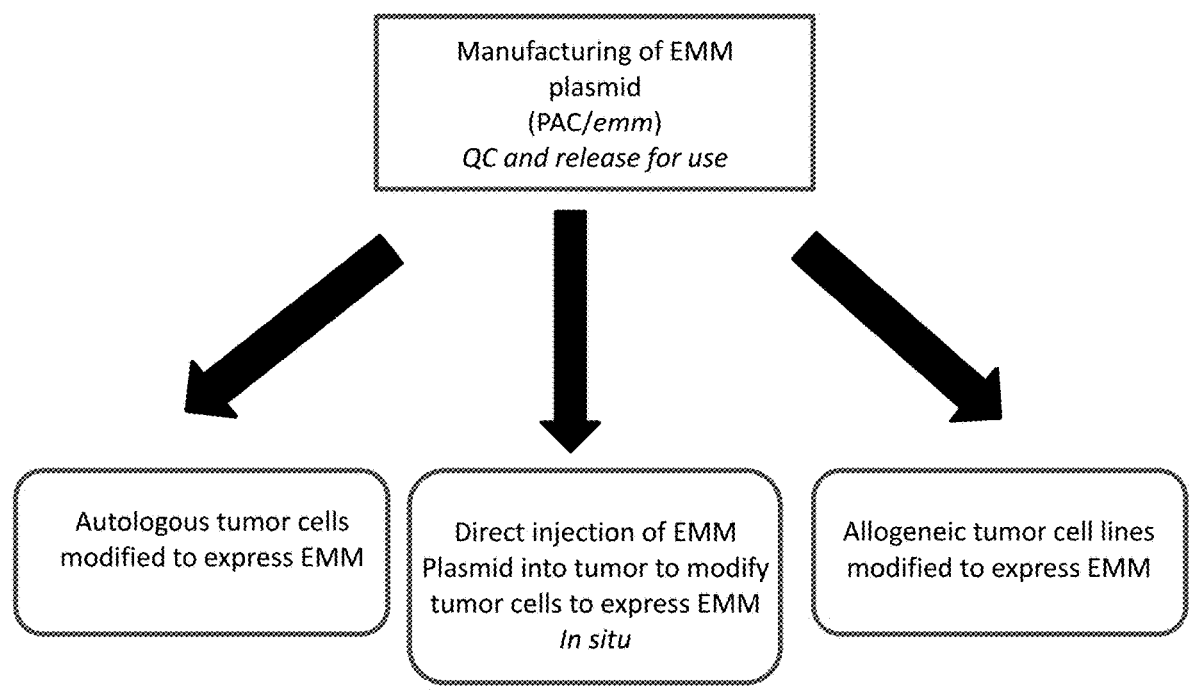
FIG. 1 is a schematic showing production of three different types of Emm vaccines.
Figure 2:
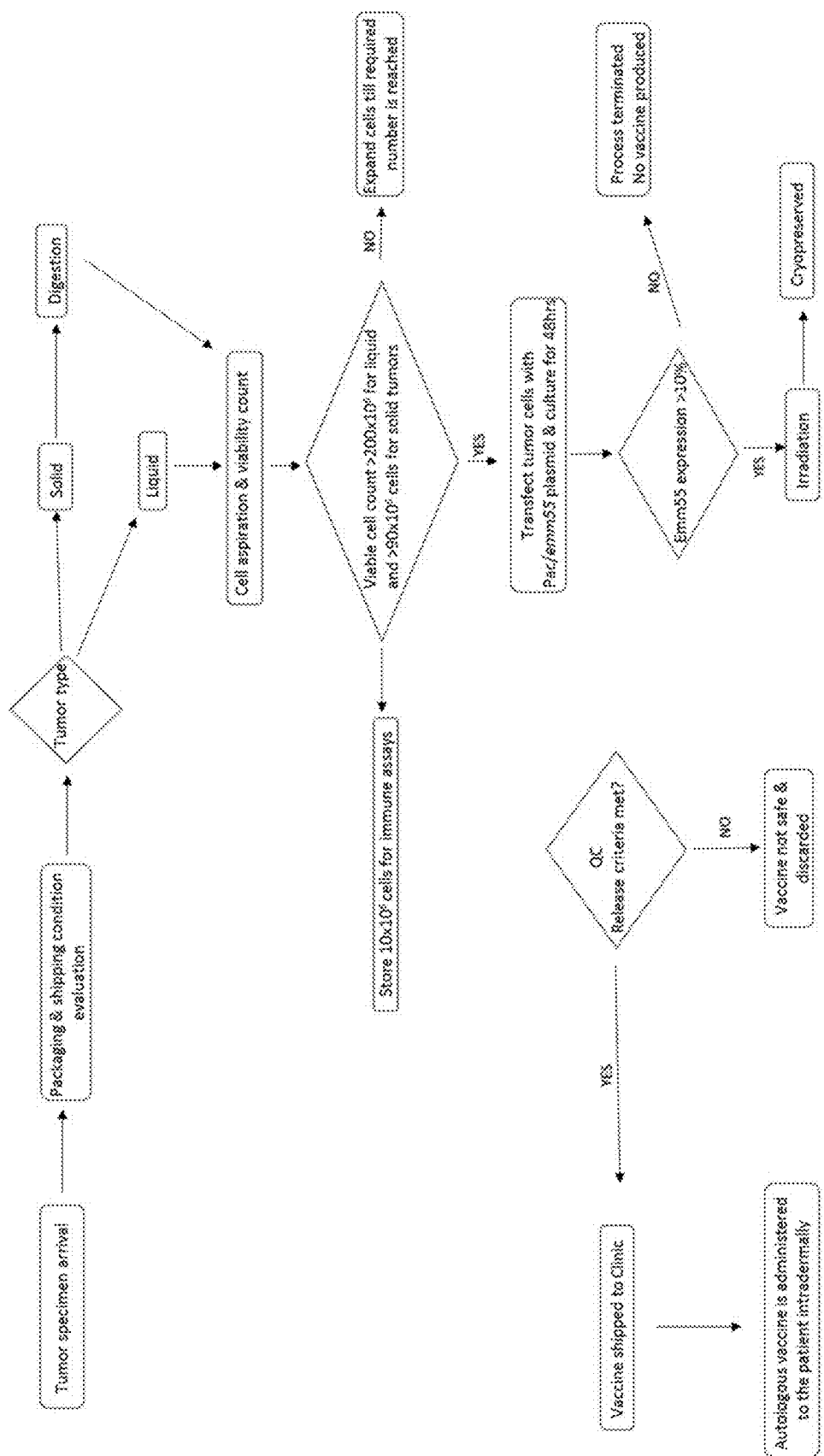
FIG. 2 illustrates the process for preparation of an Emm autologous whole cell vaccine.
Figure 3:
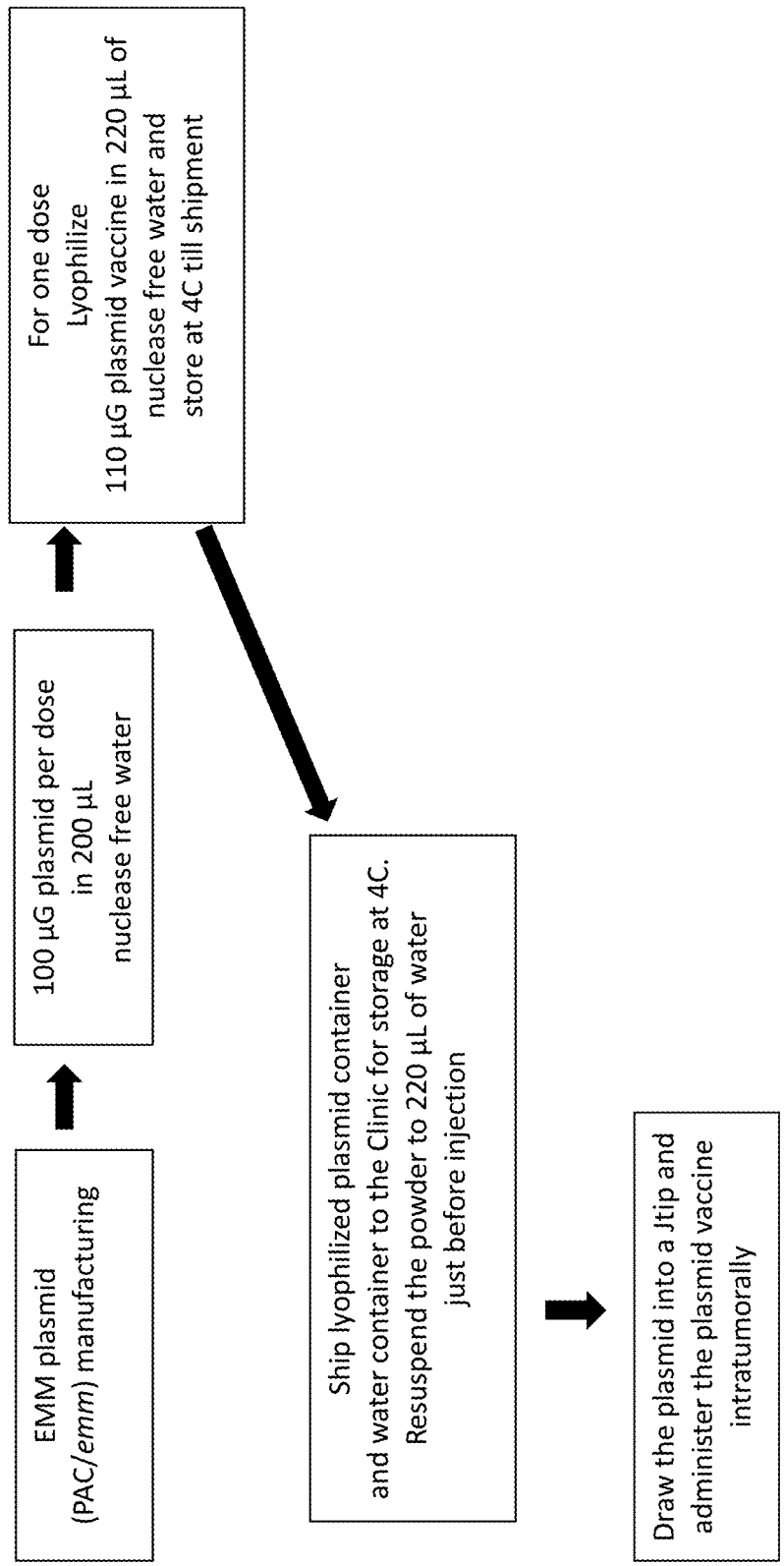
FIG. 3 shows the process for preparation of an Emm plasmid DNA vaccine.
Figure 4:
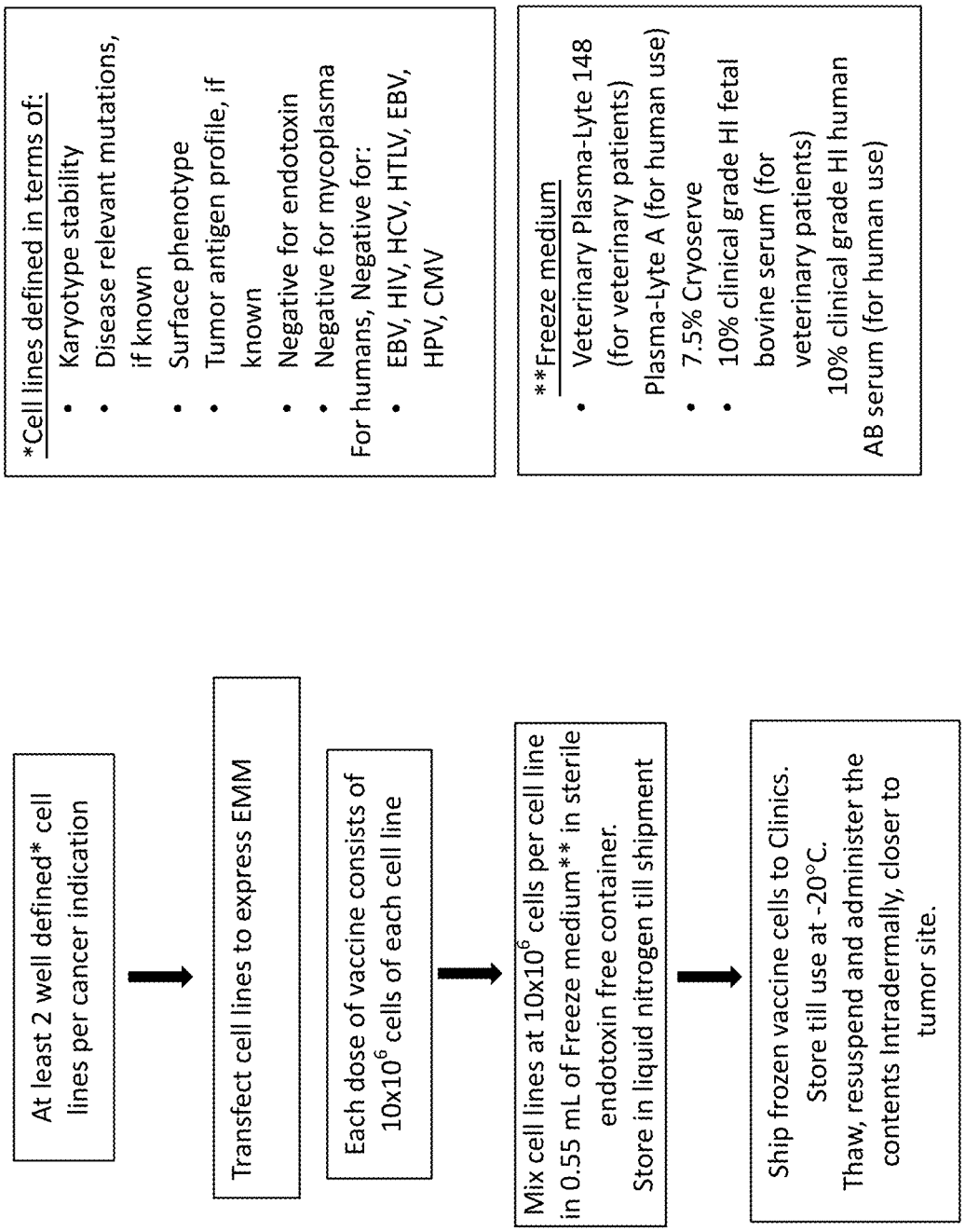
FIG. 4 shows the process for preparation of an Emm allogeneic whole cell vaccine.

The present invention provides Emm therapeutic DNA vaccines and methods for use in stimulating anticancer immunity in cancer patients. Exemplified are Emm DNA therapeutic vector injections into solid tumors in vivo and several variations of whole cell Emm vaccines, including autologous and allogeneic vaccines.

The described methods relate to the generation of whole cell tumor vaccines, prepared either in vitro (Emm expressing autologous or allogeneic cells) or generated in vivo/in situ (emm plasmid DNA administered intratumorally). The whole cell vaccine has the advantage of activating antitumor CD8+ T cells via direct and indirect (cross-priming) pathways. Whole tumor cell vaccines are considered superior to other types of vaccines because they present a plethora of tumor antigens (known and unknown) to the immune system. An overview of metastatic colon cancer immunotherapy trials has demonstrated a higher clinical benefit rate with whole cell vaccine (46%) compared to dendritic cell based (17%), peptide (13%) or idiotype antibody based (3%) vaccines. In a meta-analysis of tumor vaccines encompassing multiple cancers, Neller et al. (Seminars in Immunology, 2008, 20: 286-295) concluded that whole cell tumor vaccines provide objective clinical responses in 8.1% of patients compared to that of 3.6% with defined antigens.

In general aspects, the invention relates to methods designed to promote an immunogenic response to whole tumor cells using a therapeutic emm DNA vaccine. The vaccine can be used as autologous whole cell vaccines, direct plasmid vaccines given intratumorally, and as allogeneic whole cell vaccines.

It is also likely that the epitopes that reside within variable, hypervariable and conserved regions of M protein have been preserved across multiple M proteins. At least 2 known epitopes described in the literature are found in both the Boyle emm55 and other emm sequences. For example, two sequences of an EMM protein described as immunogenic epitopes in the mouse are conserved in both sequences (highlighted as "mouse epitope"). A potential linear B cell epitope described in humans uses M1 (EMM1) peptides which react with sera. When aligned, the M1 sequence has only 5% coverage of emm sequence suggesting substantial differences between both genes. However, there is 55% identity at the epitope region (highlighted as "potential human epitope") in both Emm55 and Emm sequences. Therefore, although all the M proteins do not have the same amino acid sequence, many of them will have preserved immunogenic epitopes.

The natural immunogenicity of Emm proteins is important in the formulation of the described Emm vaccines. The expression of the protein in tumor cells greatly increases tumor cell immunogenicity, which in turn promotes activation of both innate and adaptive antitumor immunity. A clinically meaningful response against tumor cells, such as tumor regression/prevention of recurrence results from in vivo activation of the immune system.

Due to the nature of the coevolution of microbes and the immune system, with constant selection pressure applied bilaterally, microbial products have special impact on the innate and hence adaptive immune system via pathogen recognition receptor (PRRs) and toll like receptors (TLRs). By these mechanisms, the microbial products can deliver the required "danger" signal, and robustly activate the immune system. Therefore, the Emm based cancer vaccines are more capable of inducing a clinically meaningful antitumor immunity.

*S. pyogenes* bacteria are recognized as foreign by APCs, including dendritic cells (DCs). The innate immune system is activated through a coordinated interplay between MyD88-independent events involving phagocytosis and antigen processing as well as MyD88-dependent signaling pathways involved in the induction of DC maturation and cytokine production. DCs deficient in signaling through each of the TLRs reported as potential receptors for gram positive cell components, such as Toll-like receptor (TLR)1, TLR2, TLR4, TLR9, and TLR2/6, are not impaired in the secretion of pro inflammatory cytokines and the upregulation of costimulatory molecules after S. pyogenes stimulation. This implies a multi model recognition in which a combination of several different TLR-mediated signals are critical. Emm protein may also initiate a vigorous immune response by activating innate immunity via a TLR system when tumor cells are modified to express Emm in cancer patients in situ by direct emm vector administration intratumorally, or administered as whole cell cancer vaccines, either as autologous or allogeneic.

The ability of Emm protein to activate innate immunity and adaptive anti-tumor immunity makes this protein an ideal base for producing autologous (patient's own) tumor cells modified to express Emm. Manufactured emm gene-containing plasmid DNA can be administered directly into a tumor (in situ). Emm-expressing disease-matched, pooled cancer cells can be prepared from defined allogeneic cancer cells. These types of Emm vaccines will aid in the management of multiple cancers and can be used in conjunction with conventional standards of care, both in humans and in veterinary patients.

A highly important factor that will determine outcome for any cancer vaccine in the clinical setting lies in an ability to clear the tumor bed of the immunosuppressive environment created by tumor/secreted factors. Tumor microenvironment in multiple cancers is occupied by cells that are known to attenuate antitumor responses, such as T regulatory (T regs) cells, tumor associated macrophages and myeloid derived suppressor cells.

Such situations often result in the appearance of vaccine-induced immunity in the periphery, but not in the tumor bed, and hence are clinically irrelevant. Because Emm protein is a microbial product, it improves immunity by inducing the ingress of vaccine-activated APCs into the tumor draining lymph nodes and alerts the immune cells residing in that lymph node with a "danger" signal. All three described Emm vaccine methods are effective in this process. The various Emm treatment methods described will aid in the management of multiple cancers along with their standard of care, both in humans and in veterinary patients. The methods for producing and using the Emm vaccines are applicable for treatment of all solid and liquid tumors that can be surgically removed (autologous and allogeneic) or that can be accessed, either by palpation or by using equipment such as ultrasound and CT (direct DNA).

The disclosed Emm cancer vaccines can also be used in conjunction with monoclonal antibodies to checkpoint inhibitory molecules such as CTLA-4, PD-1, PD-L1, PD-L2, LAG3, TIM3, TIGIT; antibodies to costimulatory molecules such as CD40, OX40; antibodies capable of regulating T regs such as anti-GITR and pan anti-BCL-2; or cytokines such as IL-2, TNF-α, IFN-γ, IFN-β, and TLR agonists. The emm vector can also be used comprising additional nucleic acid that expresses immunologic molecules such as cytokines IL-2, IL-12, IL-18 and MHC genes. These will augment anti-tumor immunity.

Materials and Methods

The original emm55 gene (SEQ ID NO: 3), expresses a protein derived from the M serotype 55 group A streptococci isolate A928, termed "Emm55 or M55", which has an amino acid sequence typical of M-like proteins. The N-terminal variability of M proteins generates more than 200 distinct genotypes as determined by molecular typing. Due to their immunogenicity, M proteins have also been considered as vaccine targets against GAS infections.

The S. pyogenes emm gene used in the examples illustrated here codes for an expressed Emm protein and includes the signal and anchoring sequences (SEQ ID NO: 1). The original emm55 gene sequence (SEQ ID NO: 3) was published by Boyle, et al. in 1995 (*Molecular Immunology.* 32: 9, 669-478).

FIG. 13 and FIG. 14 show a comparison between the Boyle's published emm55 gene and the emm gene used in the examples described herein.

The emm nucleotide sequence used in the DNA vector examples exhibits high identity to Boyle's emm55 sequence and high identity in the expressed protein sequence. Despite high identity, the protein expressed from the disclosed DNA vector has an additional 15 amino acids of the plasmid frame work inserted into Emm protein due to a missense mutation of stop codon TAA to GAA in emm gene.

EXAMPLES

The following examples are provided as illustrations of the invention and are in no way to be considered limiting.

Example 1. Emm Transfected Lymphoma Cells as Vaccines

This example illustrates use of an Emm autologous whole tumor cell vaccine. The vaccine was prepared from tumor cells isolated from a canine lymphoma patient. The cells were then modified/transformed in vitro with a pAc/emm plasmid DNA before formulation into a vaccine composition and used for treatment.

A 6 year old intact male German Shepherd, was diagnosed with canine lymphoma in late March 2012. He first presented with generalized lymphadenopathy; and the lymphoma diagnosis was confirmed via fine needle aspirates of the prescapular lymph nodes. Due to an intolerance of prednisolone and other traditional medications, the owner elected autologous vaccine therapy. In late April 2012, a prescapular lymph node was surgically removed and submitted for histopathology and autologous vaccine preparation. The histopathology results indicated high grade lymphosarcoma with a guarded prognosis for survival. From the remaining lymph node tissue, $2.9 \times 10^9$ cells with 100% viability were collected. Forty eight hours post transfection, $86 \times 10^6$ viable transfected cells were collected and irradiated. Eight vaccine doses were prepared for administration.

In late April 2012, the Shepherd received the first four vaccines intradermally once weekly for 4 weeks. After administration of each of the first four vaccines, the owner reported an increased energy level that lasted 5-6 days. At the request of both owner and clinician, the Shepherd received the last four vaccines intradermally every 2 weeks. At the time of the $7^{th}$ vaccine, owner reported that his appetite and energy level had improved. The Shepherd received the eighth vaccine early July 2012. Two weeks later, the clinician reported that his appetite was "waxing and waning" and his energy level was moderate.

Figure 5:
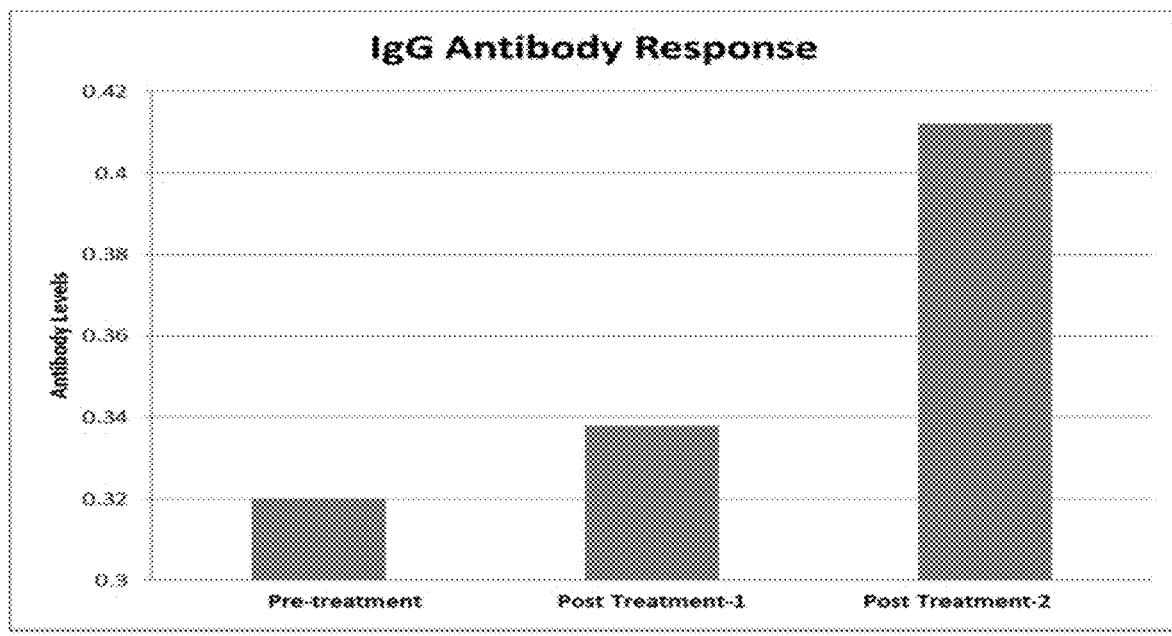
FIG. 5 compares IgG antibody levels before treatment, after 4 injections and after 8 injections.

The Shepherd died Oct. 5, 2012. The clinician reported that the traditional prognosis for this dog was only 4-6 weeks with no therapy. Thus, the overall survival was prolonged by 6 months. Based on the clinician's assessment, an improved QOL was achieved during the remaining 6 months of his life. The improved survival and QOL were associated with the induction anti-tumor antibody responses (FIG. 5).

Evidence of induction of an anti-tumor immune response was determined using autologous whole cell lysate in an Enzyme-Linked Immunosorbent Assay (ELISA). The purpose of the ELISA was to determine the titer of the anti-tumor antibodies present in a sample and if so, how much. ELISAs were performed in 96-well plates which permits high throughput results.

The bottom of each well was coated with tumor proteins, which bind the antibodies to selected proteins. Proteins from the Shepherd's tumors were used. Whole blood was centrifuged out to obtain the clear plasma, a source of antibodies. When the enzyme reaction was complete, the plate was placed into a plate reader and the optical density determined for each well. The color produced was proportional to the amount of primary antibody bound to the tumor proteins on the bottom of the wells.

The ELISA test results using the Shepherd's blood showed that the antitumor antibody response of IgG isotype was induced and continued to be boosted by the injections of processed autologous cancer cells, indicating an active ongoing anti-tumor immunity.

Example 2. In Vivo emm DNA Vector Delivery into a Solid Tumor

In contrast to the whole cell Emm vaccine in Example 1, an emm plasmid was delivered intratumorally in this example. This type of therapeutic DNA vector vaccine is applicable in multiple types of cancers to induce robust anti-tumor immunity. The following illustrates the preparation and use of a naked plasmid DNA vaccine.

Mammary adenocarcinoma cells were transformed in vivo by intratumoral delivery of a DNA vector expressing Emm protein.

A female Golden retriever mix afflicted with mammary adenocarcinoma became a candidate for Emm-based plasmid vaccine under the supervision of her attending veterinarian. She was 6-10 years old (exact age unknown) and weighed 69 lbs. Her expected longevity was 3 months. She had a tumor mass (32.3 mm×30.8 mm) on the left cranial thoracic gland and several lesions on the lungs as per X-ray. This patient was terminally ill with a huge tumor burden at the primary site (mammary gland) and several metastasized lesions in the lungs. The patient did not receive prior or concurrent therapy.

The Retriever was injected intratumorally with 300 μg of pAc/emm plasmid DNA using a needless injector in 600 μL of endotoxin/nuclease free water. Due to the large size of the mammary tumor, vaccination was equally divided and administered into three different sites of the same tumor. A total of eight intratumoral injections were given at two week intervals. Tumor measurements were made prior to each injection time point. No attempt was made to include measurement of lung lesions as per the owner's request due to cost.

Blood samples were obtained at several pre and post injection time points in order to determine antibody and T cell responses. Three weeks after the eighth vaccination, the tumor mass was surgically removed and processed.

Figure 6:
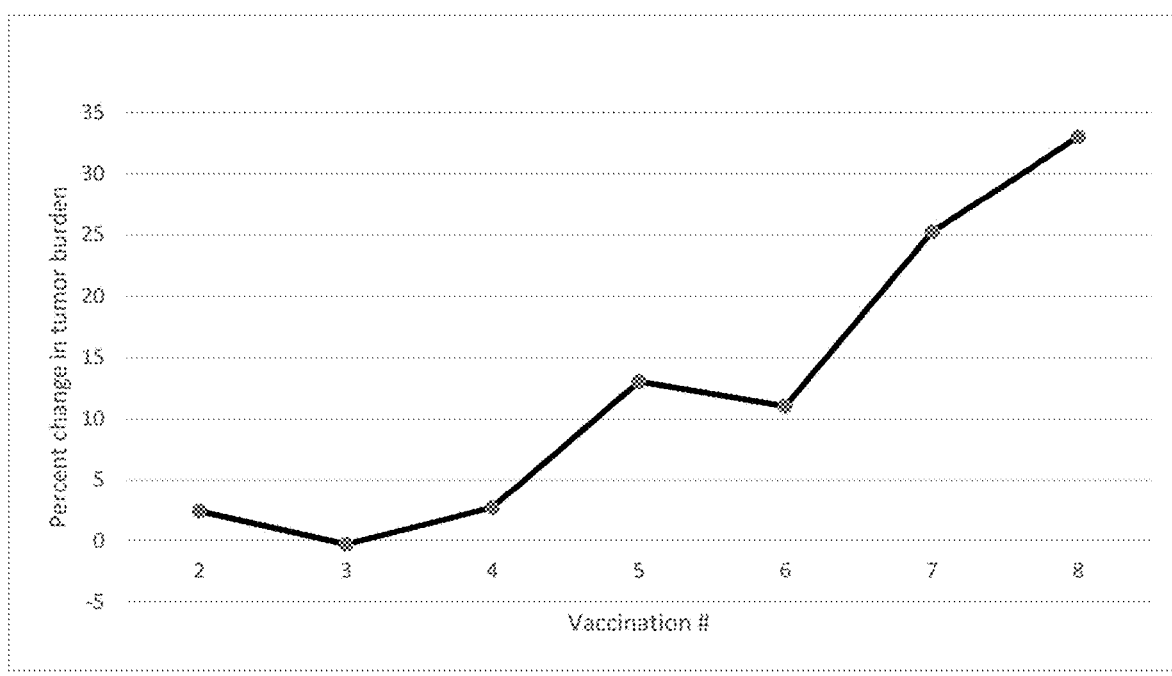
FIG. 6 shows the primary mammary tumor burden in canine patient. Overall tumor burden was stable until the 5$^{th}$ vaccination with only 11% change in tumor mass, after which, at the time of 8$^{th}$ injection, tumor size had increased by 33%, thus becoming a progressive disease.

Although the overall tumor burden increased over time, this was in part due to the presence of tumor infiltrating lymphocytes (see below) (FIG. 6).

Figure 7:
FIG. 7 shows a quality of life (QOL) assessment by the pet owner. The number on the x-axis represent $3^{rd}$, $5^{th}$ and $8^{th}$ vaccination time points at which QOL assessments were provided.

It is known with immunotherapies that tumor masses may increase in size and then regress. An X-ray taken two weeks after the last vaccine injection showed increased lung lesions. However, patient QOL, as assessed by the owner, at third, fifth and eighth injection time points remained consistently good (FIG. 7). The resected tumor mass from the primary site of the mammary tumor (three weeks after the eighth injection) was digested with enzyme mix and assessed for hematopoietic cells using anti-canine CD45-FITC conjugated antibody.

Figure 8:
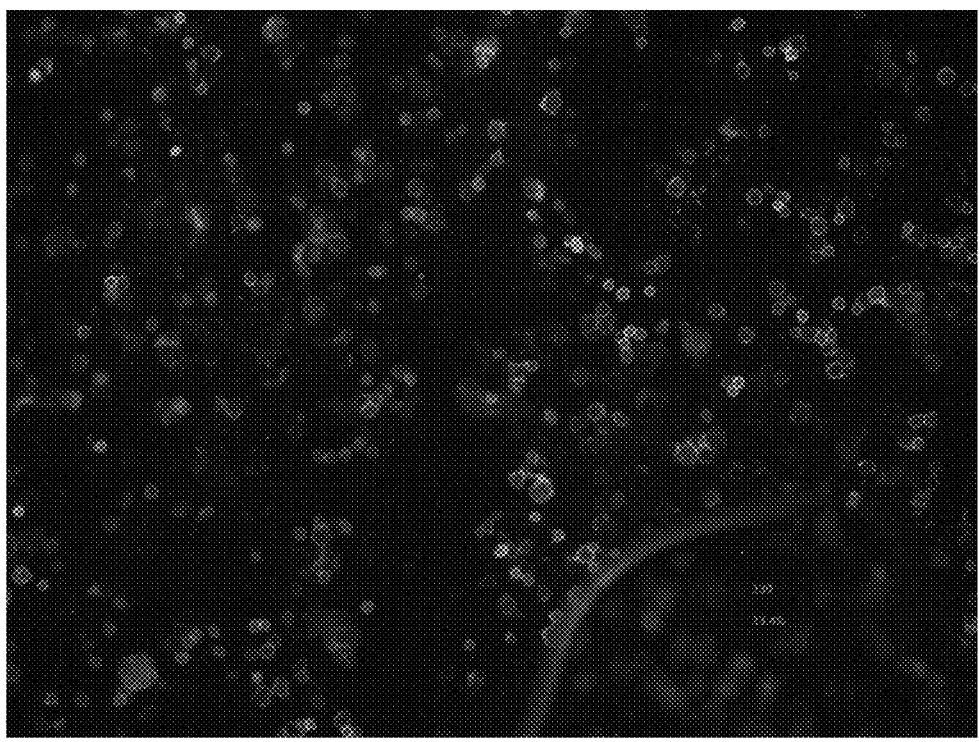
FIG. 8 shows that CD45+ hematopoietic cells were present along with tumor cells. More than 33% of the cells were CD45+ cells, suggesting a robust infiltration of immune cells into the tumor.
Figure 9:
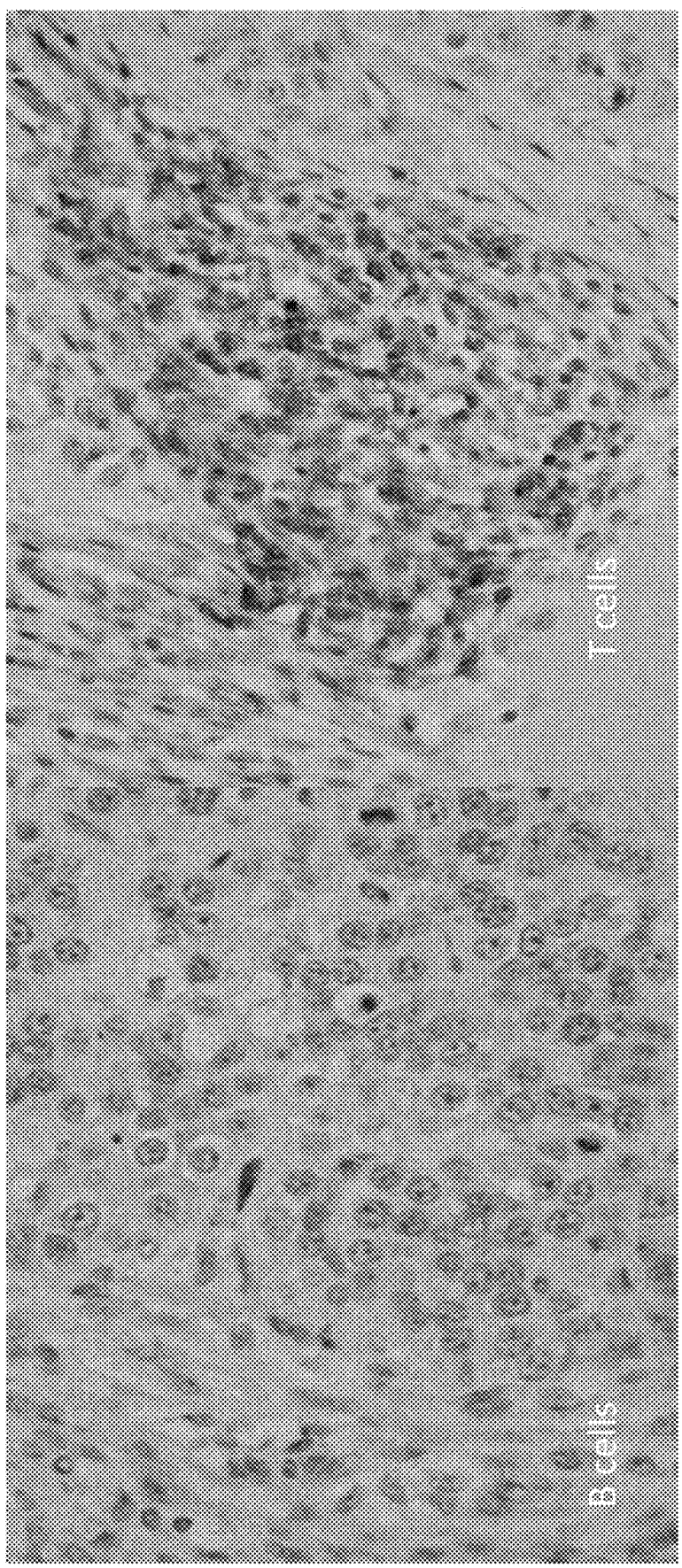
FIG. 9 shows the presence of T and B cells in the primary canine mammary tumor.

In the processed tumor cells, more than 33% of the cells were CD45+ (FIG. 8). Immunohistochemistry of the tumor tissue also demonstrated the presence of both T and B cell in the tumor and stromal (FIG. 9). By comparison, in one published seminal study, human breast cancer patients whose tumor contained >5% of intratumoral $CD45^+$ cells exhibited improved prognosis. While it is difficult to correlate human observations with that of canine mammary tumors without a well-designed clinical trial, the data show that injections with Emm55-based plasmid DNA vaccine stimulated the immune system, and that immune cells had migrated to the primary tumor.

Figure 10:
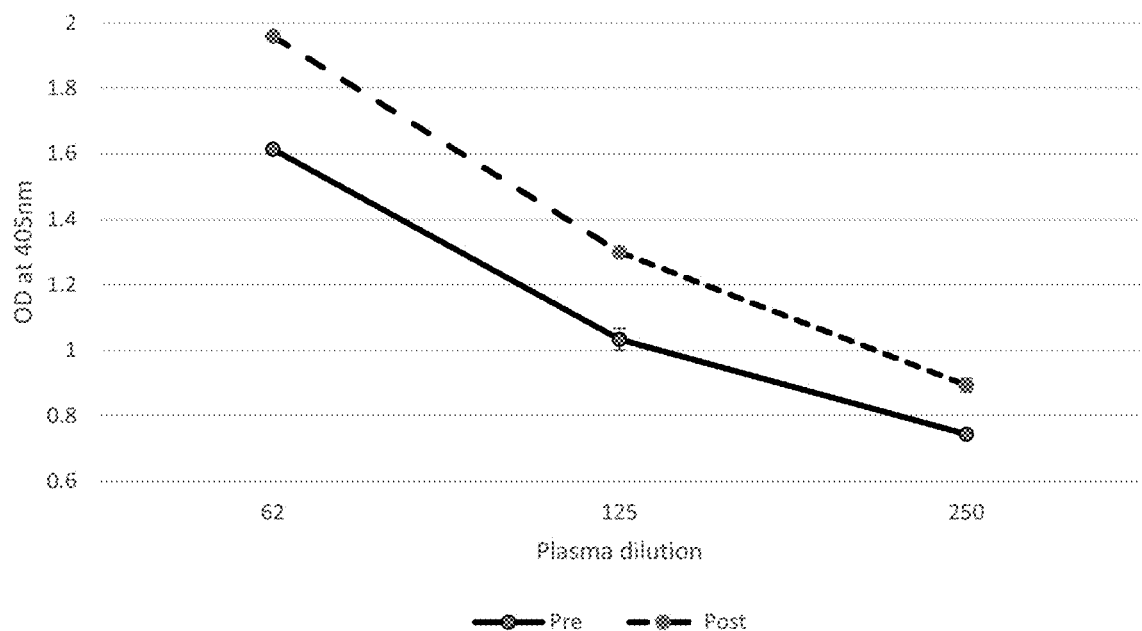
FIG. 10 shows that the antibody titer to tumor cells increased vaccination. In all three dilutions of the plasma, the antibody levels are significantly higher than pre vaccination plasma.

Preliminary analysis of the antibody response to the primary mammary tumor cells demonstrated increased antibody levels (FIG. 10). The Retriever was euthanized 6 months post initiation of vaccine therapy due to a breathing issue (laryngeal hemiplegia) and seizures. No postmortem diagnosis was carried out to determine the causes of seizures and laryngeal hemiplegia at the pet owner's request. The digested lung masses contained <2% CD45+ cells. Taken together, the Retriever's overall survival was significantly extended, three months more than she was initially assessed to live without treatment. Her QOL remained good for five months.

This case illustrates several important factors to take into account. First, one needs to consider the initial tumor burden. In the Golden Retriever's case, the burden not only was excessive at the tumor site but also showed metastasized lesions. Increased survival might be expected with earlier detection.

It is also noted that the vaccine dose used in this example was arbitrarily chosen based on an earlier study in an equine.

Example 3. In Vivo Delivery of Plasmid Expressing Emm into Multiple Lesions

This example illustrates the transformation/modification of tumor cells in situ through intratumoral delivery into multiple melanoma lesions.

A 19-year-old castrated male Arab/Quarter horse presented with an extensive history of cutaneous melanoma that had metastasized to the prescapular lymph nodes. At eight years of age, histopathology confirmed his presenting lesions to be melanoma. For the next four years, the patient's disease was stable. Between twelve and sixteen years of age, the number of this patient's melanoma lesions increased and were treated with cimetidine from time to time. He was also given an injection of an undefined vaccine from Canada at age fourteen. Tumor lesions were removed from the left flank, right hip, and right neck. However, by the age of sixteen, melanoma recurred at one of the prior surgical sites, and new cutaneous lesions were observed on his tail and neck, within his mane, and at other sites including the perianal region. Some of these lesions progressed to open sores that secreted a dark fluid exudate which later was shown to contain malignant melanocytes.

Several years prior to treatment with the therapeutic emm DNA vector, the patient was again treated surgically by removing both cutaneous lesions and lesions in the genital region. Results from blood work performed in June 2010 were normal except for a high level of lactate dehydrogenase (LDH), 569 U/L. As the severity of the disease progressed, the option for further surgery was declined, and other treatments were sought. By March 2011, no reduction of tumor burden had been noted, and the prescapular lymph nodes were beginning to become enlarged. Blood analysis completed in May 2011 indicated a high LDH level of 606 U/L, implying that the disease was still progressing. By June 2011, the patient developed a fever, and the prescapular lymph nodes continued to enlarge. The exudate fluid removed from the lymph nodes revealed high numbers of melanocytes and was contaminated with bacteria. In August 2011, the horse's illness progressed still further.

The melanoma continued to progress, and euthanasia was considered. Considering the failure of all previous treatments to control or halt the progression of the melanoma, as well as the severity and late stage of the disease, it was determined in December 2011 that the horse was a candidate for an experimental treatment that involved the direct injection of a DNA cancer vaccine.

Under strict veterinary supervision and control, the horse was treated intratumorally with a plasmid DNA vaccine. The plasmid vector pAc/emm consisted of a mammalian expression vector backbone and the 1.6-kb emm gene insert. The rationale behind the intratumoral injection of the plasmid DNA was to modify/transform melanoma tumor cells in situ. The expression of this bacterial protein on the surface of tumor cells overcomes the inherent self-tolerance to tumor antigens.

The treatment, which commenced in December 2011, involved the direct injection of plasmid DNA into cutaneous lesions. Three visible tumor masses were selected for treatment: 1 on the right side of the neck, 1 on the right side of the rump, and 1 on the tail. Two masses, one in the region of the mane and one on the tail, served as control lesions and did not receive the DNA cancer vaccine. The former three melanoma lesions were each injected with 100 µg of pAc/emm, for a total of 300 µg of plasmid DNA in a volume of 200 µL of endotoxin and nuclease-free distilled water, using a needless injector system at each vaccination time point. A total of eight plasmid DNA vaccinations were administered to each of the three lesions. The vaccine doses were administered on days 1, 19, 55, 79, 110, 145, 187, and 255. Responses were studied until the 289th day. The lesions were measured prior to injections.

The Syrijet injector is a precision instrument safely used for applying operative and surgical anesthetic for dental procedures. This was the first time this device was used for intratumoral delivery of a DNA therapeutic vaccine.

There were no inflammatory reactions at any of the injections sites throughout the course of the treatment. The size of the tumor lesions (both injected and noninjected) were measured before and after each of the DNA cancer vaccine administrations. Assessment of tumor size was carried out following published guidelines for the evaluation of immune therapy activity in solid tumors.

Figure 11:
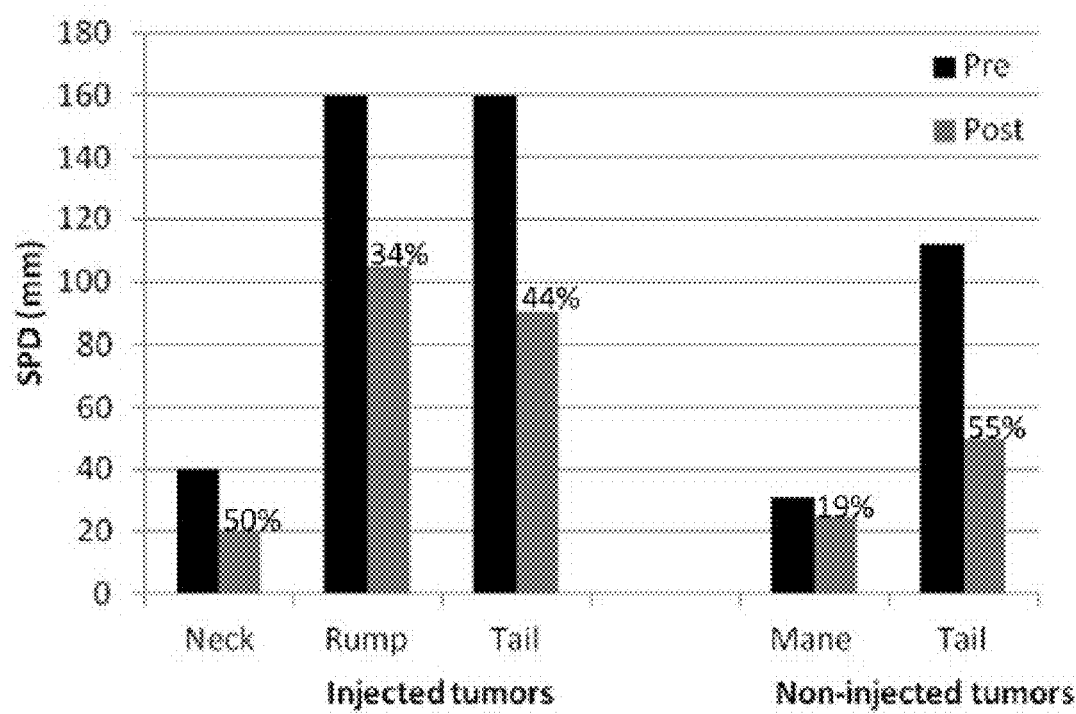
FIG. 11 shows regression of tumor lesions during the post vaccination regimen. Vaccine doses were administered on days 1, 19, 55, 79, 110, 145, 187, and 255. Responses were studied until the $289^{th}$ day. Lesions were measured prior to injections. All index lesions were measured, and the percent of reduction of tumor size was calculated for injected and noninjected lesions before treatment (black bars) and 2 weeks after the eighth vaccination (gray bars). The percent reductions observed during the post vaccination regimen are indicated above the gray bars. Reductions ranged from 19% to 55% of the original tumor size.

At the baseline and subsequent tumor assessments, all indexed lesions were measured, and the sum of the products of the two largest perpendicular diameters (SPDs) was calculated. The SPDs of the lesions were added together to provide the total tumor burden. Table 1 shows all individual measurements of indexed lesions (injected and noninjected). As shown in Table 1, there were fluctuations in the size of individual tumors, which may be due to the ingress and egress of immune cells but resulted in an overall reduction in tumor burden by the conclusion of the treatment. FIG. 11 shows the pretreatment and post measurement of individual indexed lesions along with observed percent of reductions in the mass above each bar.

Table 2 summarizes the total reduction in injected and noninjected lesions at the conclusion of the treatment regimen. Based on these data, the SPD of all injected lesions was reduced by 40.3% and that of noninjected lesions was reduced by 47.6%, with an overall reduction in tumor burden of indexed lesions by 42.3%. When all tumor measurements were combined from both the 3 treated lesions and the 2 untreated lesions, pre- and post-vaccinations, the reduction observed in tumor size reached statistical significance in a paired t test (P=0.0272).

During the course of this study, it was determined that all of the tumor masses observed stabilized, regressed in size, and ceased leaking the dark melanocyte-containing exudate. The consistency of several of the melanoma lesions went from firm to soft. By the end of September 2012, the patient had gained weight, was alert, and was healthy enough to be ridden.

TABLE 1

Measurement of tumor lesions during the study period

| Measurement | Injected Lesions (mm) | | | Noninjected Lesions (mm) | |
| --- | --- | --- | --- | --- | --- |
| | Neck | Rump | Tail | Mane | Tail |
| 1 (pre-treatment) | 40 | 160 | 160 | 31 | 112 |
| 2 | 30 | 144 | 90 | ND | ND |
| 3 | 30 | 120 | 157 | ND | ND |
| 4 | 26 | 140 | 83 | ND | ND |
| 5 | 30 | 250 | 140 | 30 | 87 |
| 6 | 30 | 168 | 75 | ND | ND |
| 7 | 23 | 223 | 105 | 26 | 45 |
| 8 | 19 | 123 | 112 | 30 | 50 |
| 9 (post-treatment) | 20 | 105 | 90 | 25 | 50 |

ND, not done

TABLE 2

Regression of injected and noninjected tumor lesions

| Tumor Lesions | Pre-treatment | Post-treatment | % Reduction |
| --- | --- | --- | --- |
| Injected | 360 mm | 215 mm | 40.3 |
| Noninjected | 143 mm | 75 mm | 47.6 |

Figure 12:
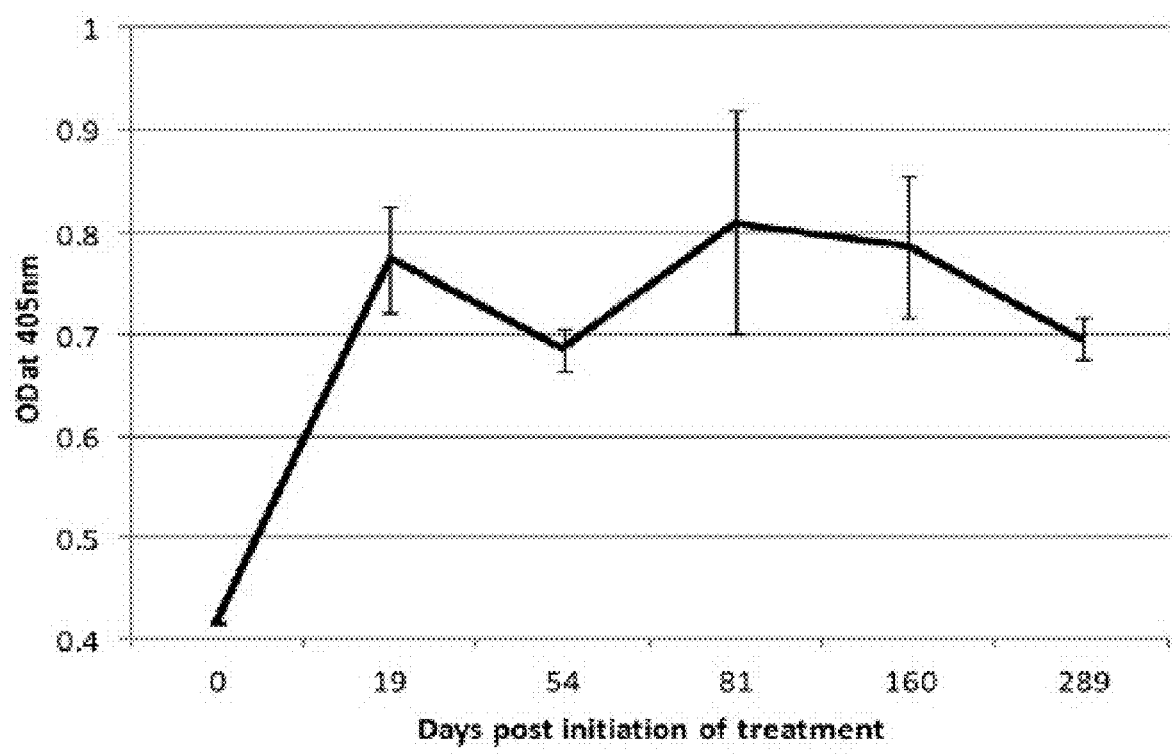
FIG. 12 shows augmentation of antimelanoma antibodies during the vaccination regimen. Vaccine doses were administered on days 1, 19, 55, 79, 110, 145, 187, and 255. Responses were studied until the $289^{th}$ day. Antibody levels were determined using ELISA. The lysate protein from a noninjected melanoma specimen was used as the antigen source at 10 μg/mL. The ELISA was developed using goat anti-equine IgG antibodies conjugated to AP enzyme and PNPP substrate. The IgG antibody level in the plasma, at a 1:160 dilution in the ELISA assay, was 2-fold increased and sustained over the course of the therapy. The error bars show the SEM of triplicate values. AP, Alkaline phosphatase: ELISA, enzyme-linked immunosorbent assay: IgG, immunoglobulin G: PNPP, p-nitrophenyl phosphate.
Figure 15:
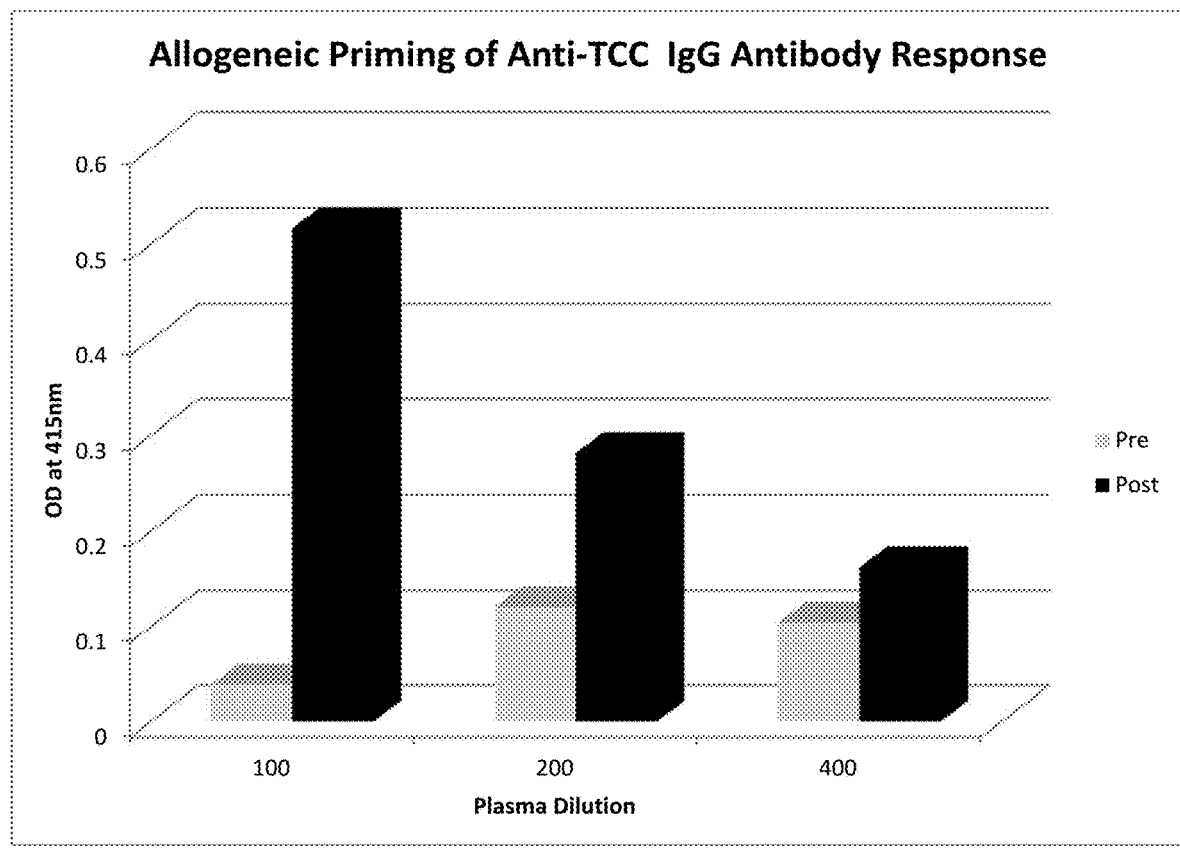
FIG. 15 shows the priming of antibody response by allogeneic whole cell vaccine.
Figure 16:
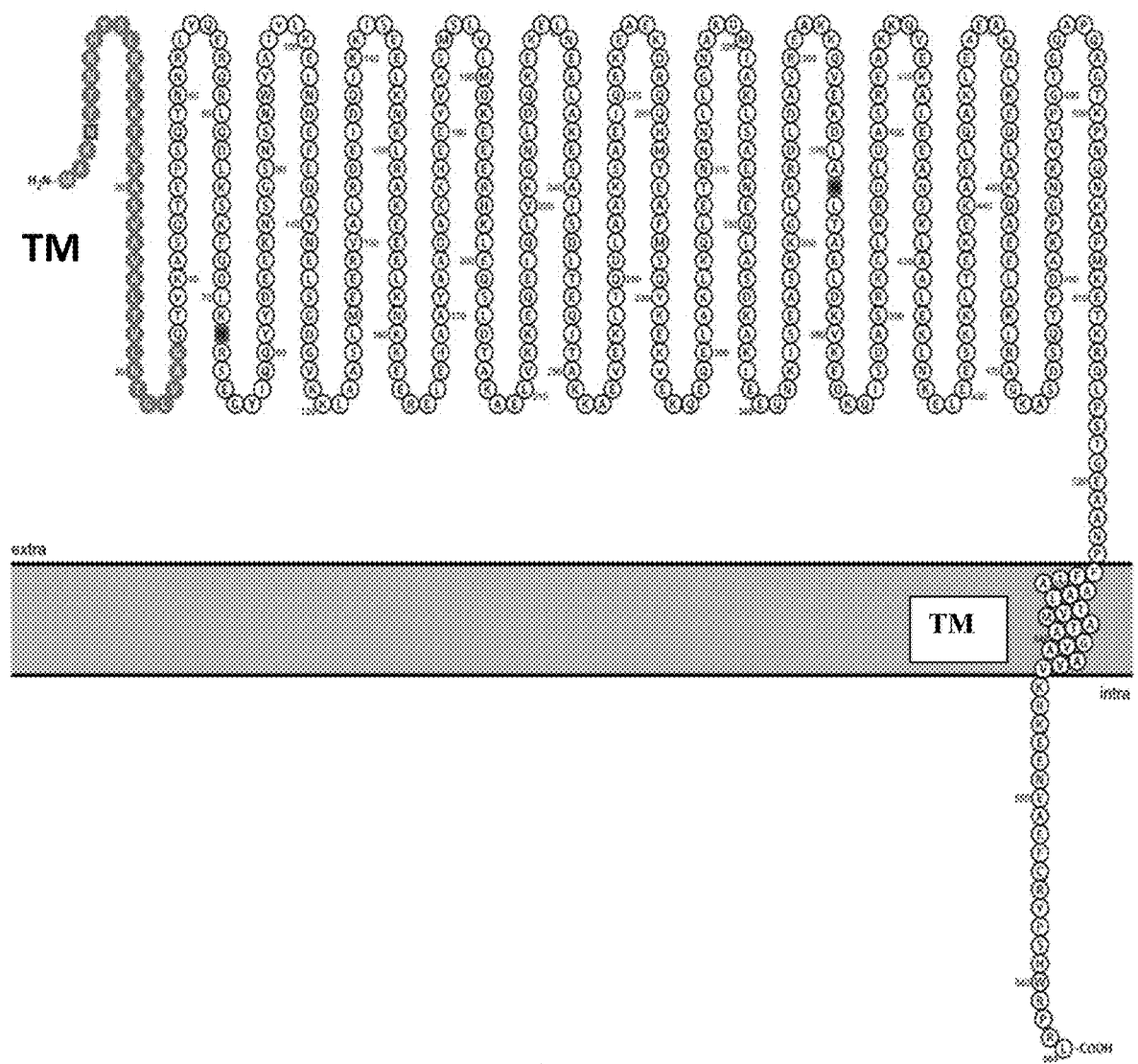
FIG. 16 is an Emm55 protein primary sequence diagram showing the TM regions of the surface expressed protein.

In order to ascertain whether the reduction in tumor burden observed correlated with the development of an antitumor immune response, antibody levels were measured using a standard ELISA. Data shown in FIG. 12 indicate that vaccination by direct injection of the DNA cancer vaccine resulted in the induction of anti-melanoma IgG antibody response which increased 2-fold over time and persisted until the end of the study.

This example demonstrates a significant clinical benefit from injecting several melanoma tumors with the Emm therapeutic DNA vector. The melanoma cells in the injected mass expressed the Emm polypeptide, became immunogenic and elicited a measurable anti-melanoma immune response and systemic tumor regression contributing to prolonged survival.

Example 4. Allogeneic Whole Cell Vaccine Treatment of Carcinoma

A male neutered 11 year old Shetland Sheepdog was presented to Morphogenesis on May 25, 2012 for whole cell vaccine therapy. He had previously been diagnosed with nonpapillary transitional cell carcinoma (CTCC) on May 4, 2012. His initial treatment included Piroxicam, a non-steriodal anti-inflammatory agent. For vaccine preparation, his bladder mass was surgically removed and submitted for autologous tumor cell processing. Due to difficulties in early expansion of autologous carcinoma cells, with the owner and his attending clinician's consent, an allogeneic vaccine therapy was considered for administration.

A previous patient's transitional carcinoma cells were processed and used to prime anti-tumor immunity. The $1^{st}$ vaccine dose contained $10 \times 10^6$ allogeneic cells. After the $1^{st}$ vaccine, the clinician reported that the Sheepdog had an increased appetite and energy level. The clinician also reported that the blood in the urine had resolved, which was an issue previously. The $2^{nd}$ through $4^{th}$ vaccines contained a mixture of both allogeneic cells and autologous cells in 80% allogeneic/20% autologous ratio. The $5^{th}$ through $12^{th}$ vaccines contained 100% autologous cells. The first 9 vaccines were administered once a week for 4 weeks. He restarted receiving the $10^{th}$ through $12^{th}$ vaccines biweekly. All doses were given intradermally. Approximately 1 year (July 2013) after initially started the vaccine regime, the owner reported that the Sheepdog was happy and had a puppy-like playfulness. In October 2013, the clinician reported that the Sheepdog became asymptomatic of his disease and his urinary bladder appeared small and less taunt. Also in October, tumor cells were collected from a urine specimen and expanded in culture. These urine tumor cells and original autologous tumor cells were used in combination to supply the $13^{th}$ through $15^{th}$ vaccines, which were administered, intradermally, on a monthly basis. The $16^{th}$ vaccine was administered one month after the $15^{th}$ vaccine and the $17^{th}$ vaccine was administered two months after the $16^{th}$ vaccine. The Sheepdog received his final vaccine, the $17^{th}$ dose, in April 2014. Prior to receiving the $16^{th}$ vaccine in February, the clinician reported that the Sheepdog had a palpable mass in the bladder that was impinging on the anus. Due to quality of life concerns, the owner elected euthanasia a few weeks later. Though he succumbed to the disease, both clinician and owner were impressed that he survived almost two years post diagnosis.

In order to evaluate the immunogenicity of allogeneic whole cell vaccine, autologous tumor specific antibodies were measured. The induction of anti-tumor immune response was determined using autologous whole cell lysate in an Enzyme-Linked Immunosorbent Assay (ELISA). The purpose of an ELISA is to determine if a particular protein is present in a sample and if so, how much. ELISAs are performed in 96-well plates which permits high throughput results. The bottom of each well is coated with tumor proteins to which will bind the antibodies one wants to measure. In this case, proteins from the Sheepdog's tumor cells were used. Whole blood is centrifuged out to obtain the clear plasma, a source of antibodies. When the enzyme reaction is complete, the entire plate is placed into a plate reader and the optical density is determined for each well. The amount of color produced is proportional to the amount of primary antibody bound to the proteins on the bottom of the wells.

Based on the ELISA test results using the Sheepdog's blood, the anti-tumor antibody response of IgG isotype had been induced and which continued to be boosted by the injections of autologous cancer cells, suggesting that initial 4 doses of allogeneic vaccines successfully induced anti-tumor immunity.

Example 5. Emm Transfected Allogeneic Cell Lines as Vaccines

The induction of robust anti-tumor immune responses is known to depend on the cross-presentation of vaccine derived TAA to specific cytotoxic T lymphocytes (CTL) in vivo. This process of cross-priming is facilitated by the activation of APCs such as DCs. Allogeneic cells are able to present a viable source of TAA, which would be taken up by DC and then presented in the context of appropriate MHC alleles to autologous CTL.

An Emm vaccine can be prepared from transfected well-defined tumor specific allogeneic cell lines by modifying/transforming tumor cell lines in vitro with pAc/emm plasmid DNA.

Example 6. Selection of Emm Transformed Allogeneic Cell Lines

Published mouse studies have clearly demonstrated that the efficacy of vaccines depends on the cross-presentation of vaccine derived TAA to specific CTL in vivo. The process of cross-priming is facilitated by the activation of professional APCs, such as DC. This suggested that allogeneic cells will also present a viable source of TAA, which would be taken up by DCs and then presented in the context of appropriate MHC alleles to autologous CTL.

For direct antigen presentation by vaccine cell lines, for example, in humans, just by matching vaccine cell lines for the HLA-A2 and/or -A3 alleles, >50% of patients should be eligible for allogeneic vaccination regimens for a given cancer. The same is true for veterinary patients (DLA-dog leukocyte antigen, FLA-feline leukocyte antigen) and a broad applicability can be achieved by deriving vaccine cell lines across breeds to cover the wider patient population.

For indirect antigen presentation (cross-presentation) of tumor antigens, which as described above is the most efficacious way to induce immune responses, there is no need for vaccine cells to match the MHC haplotype of the patients. By mixing 2 or more well-defined cell lines derived from patients with a given cancer, both TAAs and tumor specific antigens (TSA) can be presented by the allogeneic vaccine cells.

The cell lines derived from patients with a specific cancer type need to be thoroughly defined, transfected with, for example, pAc/emm plasmid, selected using G418 antibiotic and cryopreserved at low passage number to create a master cell bank (MCB). The resistance to G418 is afforded by the neomycin gene located in the pAc/emm plasmid. In the same fashion, untransfected cell lines can also be stored. The working cell bank (WCB) is then created from MCB. Cell cultures for creating vaccines can be generated from the WCB.

The cell lines for any cancer type can be defined in terms of (as part of quality control) using the following characteristics:
Karyotype stability
Disease relevant mutations, if known
Surface phenotype
Tumor antigen profile, if known
Negative for endotoxin
Negative for *mycoplasma*
For humans, Negative for:
EBV, HIV, HCV, HTLV, EBV, HPV, CMV To prepare a vaccine for a particular cancer type, two or more cell lines belonging to that cancer type, which have been characterized as per quality control, can be mixed with untransfected cells in a required proportion. For example, 10% of transfected cell lines can be mixed with 90% untransfected cell lines to give a dosage of allogeneic vaccine containing 10% of cells expressing Emm protein. For example, a dose can be 10-20×10$^6$ cells depending on the type of cancer and preclinical studies. Based on preclinical studies, the number of cell lines to be used for a selected cancer type can be fixed.

Allogeneic Emm transformed cancer cells can be shipped frozen in freeze medium or equivalents. An exemplary freeze medium is:
Veterinary Plasma-Lyte 148 (for veterinary patients)
Plasma-Lyte A (for human use)
7.5% Cryoserve
10% clinical grade heat inactivated fetal bovine serum (for veterinary patients)

10% clinical grade heat inactivated human AB serum (for human use)

Based on data obtained from Emm autologous and emm plasmid DNA vaccines, allogeneic vaccines are able to induce anti-tumor immune response, improve survival and quality of life of the patients.

Despite variations between the emm55 protein and the disclosed emm in nucleotide sequence (98% identity) and protein sequence (97.1% identity excluding 15 amino acids of the plasmid frame work), at least 3 known epitopes described in the literature are found in the both sequences. For example, the sequences of the Emm protein described as immunogenic epitopes in the mouse are conserved in both Emm and Emm55 sequences (highlighted as "mouse epitope"). A potential linear B cell epitope was described in humans using M1 (EMM1) peptides which reacted with sera. When aligned, the M1 sequence has only 5% coverage of Emm55 sequence suggesting substantial differences between both genes. However, there is 55% identity at the epitope region (highlighted as "potential human epitope") in both Emm and Emm55 sequences. Therefore, variations found between Emm55 and the Emm demonstrated herein, such variations do not significantly alter immunogenicity of the protein. Instead.

Table 3 shows that the Emm polypeptide expressed by the vector used in the examples is different from the polypeptide expressed by the emm55 gene.

TABLE 3

| Amino acid position | Emm SEQ ID NO: 2 | Emm55 SEQ ID NO: 4 |
|---|---|---|
| 10 | Tyrosine (Y) aromatic hydrophobic | Aspartic acid (D) negatively charged |
| 42 | Serine (S) polar neutral | Asparagine (N) polar neutral |
| 67 | Phenylalanine (F) aromatic hydrophobic | Valine (V) nonpolar aliphatic |
| 154 | Lysine (K) positively charged | Threonine (T) polar neutral |
| 174 | Alanine (A) nonpolar aliphatic | Valine (V) nonpolar aliphatic |
| 188 | Valine (V) nonpolar aliphatic | Alanine (A) nonpolar aliphatic |
| 195 | Glutamic acid (E) negatively charged | Serine (S) polar neutral |
| 196 | Arginine (R) positively charged | Alanine (A) nonpolar aliphatic |
| 455 | Alanine (A) nonpolar aliphatic | Threonine (T) polar neutral |
| 459 | Glutamine (Q) polar neutral | Lysine (K) positively charged |
| 490 | Valine (V) nonpolar aliphatic | Alanine (A) nonpolar aliphatic |
| 494 | Threonine (T) polar neutral | Lysine (K) positively charged |
| 512 | Threonine (T) polar neutral | — |
| 525 | Alanine (A) nonpolar aliphatic | Threonine (T) polar neutral |
| 544 | Alanine (A) nonpolar aliphatic | — |
| Amino acids found only in Emm | | |
| 552 | Glutamic acid (E) negatively charged | |
| 553 | Alanine (A) nonpolar aliphatic | |
| 554 | Glutamic acid (E) negatively charged | |
| 555 | Phenylalanine (F) aromatic hydrophobic | |
| 556 | Cytosine (C) polar neutral | |
| 557 | Arginine (R) positively charged | |
| 558 | Tyrosine (Y) aromatic hydrophobic | |
| 559 | Proline (P) polar neutral | |
| 560 | Serine (S) polar neutral | |
| 561 | Histidine (H) positively charged | |
| 562 | Tryptophan (W) aromatic hydrophobic | |
| 563 | Arginine (R) positively charged | |
| 564 | Proline (P) polar neutral | |
| 565 | Arginine (R) positively charged | |
| 566 | Leucine (L) nonpolar aliphatic | |

Example 7. Primary Sequence of Emm55 Protein Domains

The primary sequence analysis carried out using TMpred online tool available in SIB (ExPASY) indicates, as per statistical scores, that there are two potential regions of helices capable of transmembrane insertion (Table 4). One is located within N-terminal signal peptide region (SEQ ID NO: 7) and the other one is present within C-terminal GAS anchor region (SEQ ID NO: 9). As expected, N-terminal TM helix is oriented towards inside to outside (enabling egress to surface) while TM helix within the C-terminal anchor region is oriented towards outside to inside orientation to anchor the protein on the surface (FIG. 16). Surface and cytoplasmic expression of Emm55 protein in FIG. 16 and FIG. 17.

TABLE 4

Possible TM helices predicted by Tmpred
(Swiss Institute of Bioinformatics)

| From-To | Score | Region | Orientation score |
|---|---|---|---|
| 18-36 | 1591 | within N-terminal signal region | Inside to outside++ |
| 524-543 | 1385 | within C-terminal anchor region | Outside to inside++ |

Transmembrane prediction score: only scores above 500 are considered significant.
Orientation score: "++" symbol indicates a strong preference of this orientation.
Predicted C-terminal TM sequence: FFTAAALTVMATAGVAAV (SEQ ID NO: 9)

Example 8. In Vitro Expression of Emm55 Protein

Figure 17:
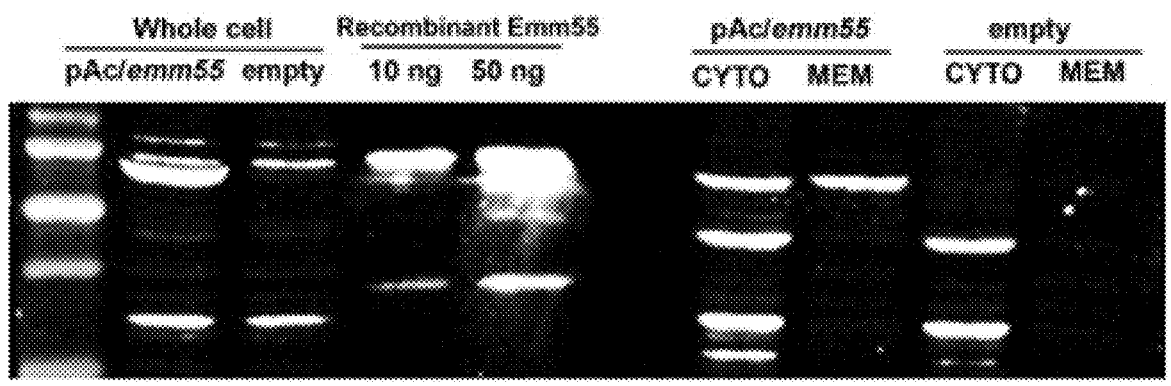
FIG. 17 is a Western blot showing expression of Emm55 in a kidney cell membrane.
Figure 18:
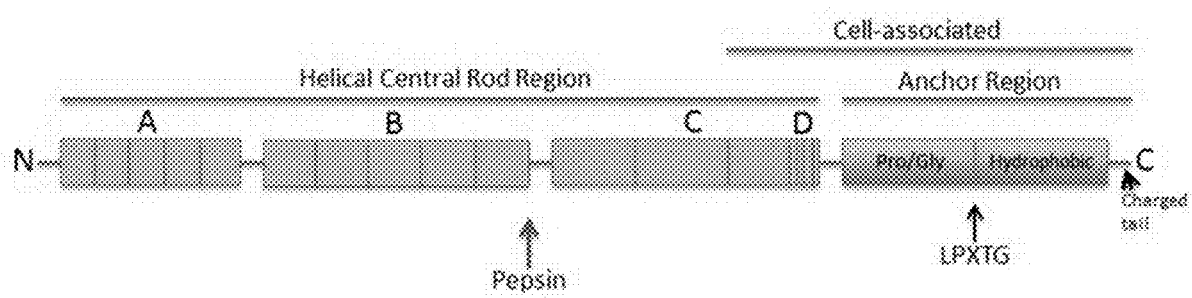
FIG. 18 shows the structure of the M6 protein.
Figure 19:
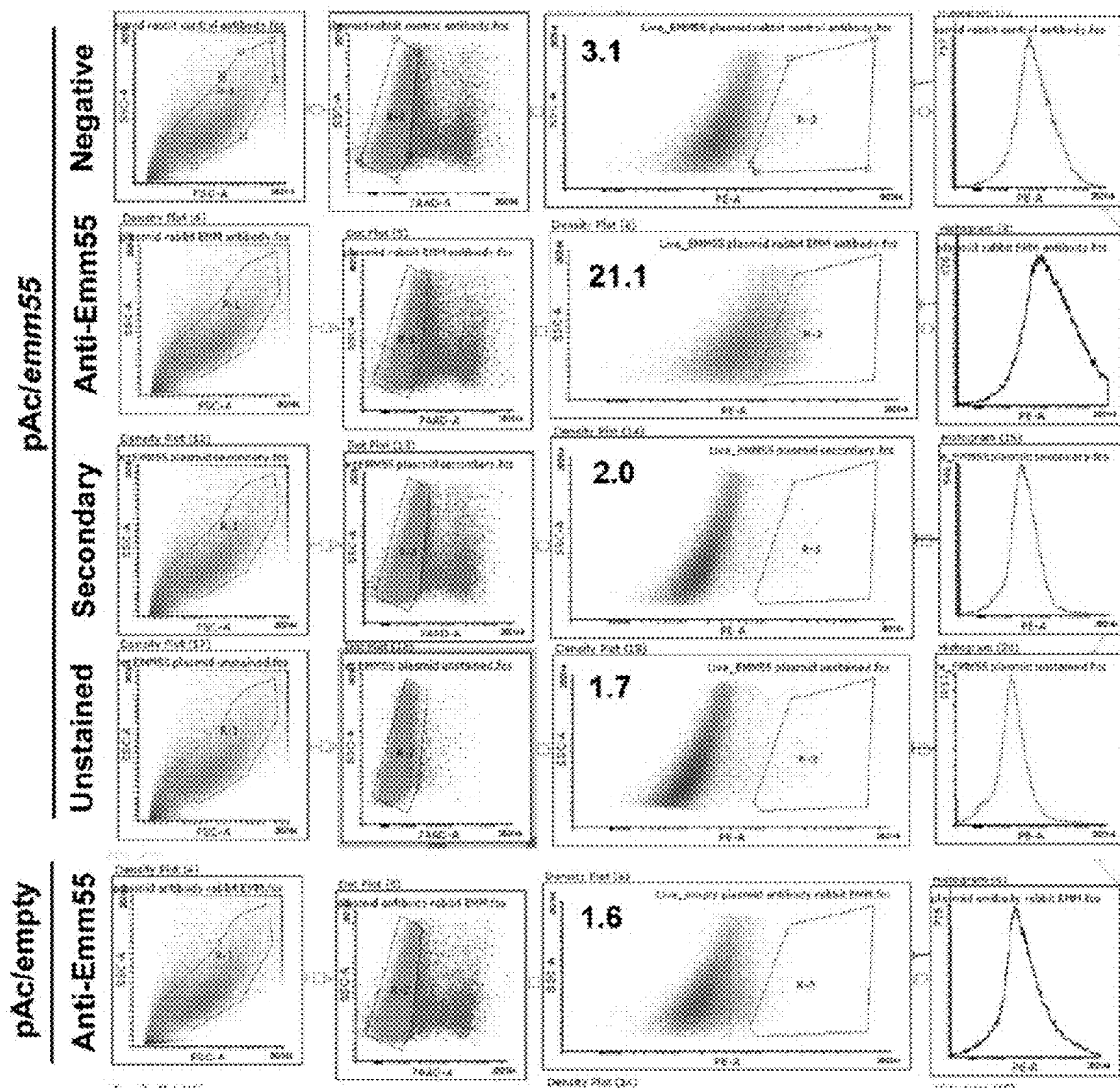
FIG. 19 shows flow cytometric analyses of surface expression of Emm55 on ~20% of transfected cells.

In vitro transfections of eukaryotic cells were used to assess the ability of pAc/emm55 to drive transcription and translation of emm55. Transient transfection of human embryonic kidney cell line HEK293T (ATCC CRL-3216) with pAc/emm55 using lipofection (Lipofectamine 2000, Invitrogen; Carlsbad, Calif.) resulted in the expression of Emm55 protein on the cell membrane and in the cytoplasm. Western blot analyses of whole cell protein and subcellular protein fractions of HEK293T cells transfected with pAc/emm55, incubated with RAB-AP01 (affinity purified rabbit anti-Emm55 peptide antibodies) then stained with anti-rabbit horseradish peroxidase, resulted in the detection of a band corresponding to the predicted molecular mass of recombinant Emm55. In subcellular protein lysates, Emm55 is detected in both the cytoplasmic and membrane fractions (FIG. 17). No protein of matching molecular mass was detected in lysates of HEK293T cells transfected with pAc/empty. Flow cytometric analysis of pAc/emm55-transfected HEK293T cells stained with RAB-AP01 resulted in a consistent positive population of ~20% when gated against a rabbit IgG negative control, an anti-rabbit-PE secondary antibody only control, unstained cells or pAc/empty-transfected cells stained with anti-Emm55 (FIG. 19).

What is claimed is:

1. A method for preparing a membrane anchoring protein, comprising:
   inserting a first DNA encoding the amino acid sequence of SEQ ID NO: 7 into the N-terminal signal region of a DNA encoding an M serotype 55 group A *streptococcus* protein;
   inserting a second DNA encoding the amino acid sequence of SEQ ID NO: 9 into the C-terminal anchor region of the DNA encoding said protein;
   wherein the encoded protein expressed from the modified DNA is a membrane anchoring protein.

2. The method of claim 1 wherein the M serotype 55 group A *streptococcus* protein is a gram positive bacterial cell wall protein.

3. The method of claim 2 wherein the gram positive bacterial wall protein is from a serotype of group A *Streptococcus*.

4. The method of claim 1 wherein the encoded protein has the amino acid sequence of SEQ ID NO: 5.

5. The method of claim 1 wherein the membrane anchoring protein anchors to a cell membrane.

6. The method of claim 5 wherein the cell membrane is a eukaryotic membrane.

7. The method of claim 5 wherein the cell membrane is a prokaryotic membrane.

* * * * *

UNITED STATES PATENT AND TRADEMARK OFFICE
CERTIFICATE OF CORRECTION

PATENT NO. : 10,751,400 B2
APPLICATION NO. : 16/551138
DATED : August 25, 2020
INVENTOR(S) : Michael J. P. Lawman et al.

Page 1 of 1

It is certified that error appears in the above-identified patent and that said Letters Patent is hereby corrected as shown below:

In the Specification

Column 2,
Line 40, "MEW" should read --MHC--.

Signed and Sealed this
Twenty-sixth Day of January, 2021

Drew Hirshfeld
*Performing the Functions and Duties of the*
*Under Secretary of Commerce for Intellectual Property and*
*Director of the United States Patent and Trademark Office*